(12) United States Patent
Porat

(10) Patent No.: US 8,956,870 B2
(45) Date of Patent: Feb. 17, 2015

(54) METHOD FOR USING DIRECTING CELLS FOR SPECIFIC STEM/PROGENITOR CELL ACTIVATION AND DIFFERENTIATION

(71) Applicant: Biogencell, Ltd., Hod-Hasharon (IL)

(72) Inventor: Yael Porat, Hod-Hasharon (IL)

(73) Assignee: Biogencell, Ltd., Hod-Hasharon (IL)

( * ) Notice: Subject to any disclaimer, the term of this patent is extended or adjusted under 35 U.S.C. 154(b) by 0 days.

(21) Appl. No.: 13/743,966

(22) Filed: Jan. 17, 2013

(65) Prior Publication Data
US 2013/0189233 A1 Jul. 25, 2013

Related U.S. Application Data

(60) Provisional application No. 61/588,228, filed on Jan. 19, 2012.

(51) Int. Cl.
*C12N 5/078* (2010.01)
(52) U.S. Cl.
CPC .................................. *C12N 5/0634* (2013.01)
USPC ............................ 435/377; 435/372; 435/373
(58) Field of Classification Search
None
See application file for complete search history.

(56) References Cited

U.S. PATENT DOCUMENTS

| | | | |
|---|---|---|---|
| 5,969,105 | A | 10/1999 | Feng et al. |
| 6,479,286 | B1 | 11/2002 | Nelson et al. |
| 7,030,228 | B1 | 4/2006 | Schmitz et al. |
| 8,709,802 | B2 | 4/2014 | Porat |
| 2005/0226852 | A1* | 10/2005 | Toda et al. .................. 424/93.7 |
| 2007/0269867 | A1 | 11/2007 | Ghosh |
| 2008/0206286 | A1 | 8/2008 | Yu |
| 2008/0226612 | A1 | 9/2008 | Treves et al. |
| 2008/0292601 | A1 | 11/2008 | Song |
| 2008/0317719 | A1 | 12/2008 | Fulga et al. |
| 2009/0004157 | A1 | 1/2009 | Kalinski |
| 2009/0131346 | A1 | 5/2009 | Sorio |
| 2010/0143311 | A1 | 6/2010 | Mizukami et al. |
| 2011/0143437 | A1 | 6/2011 | Porat |

FOREIGN PATENT DOCUMENTS

| | | |
|---|---|---|
| WO | 9853048 A1 | 11/1998 |
| WO | 2006130651 A2 | 12/2006 |
| WO | 2008140316 A1 | 11/2008 |
| WO | 2011007348 A2 | 1/2011 |

OTHER PUBLICATIONS

Balan et al. "A large number of mature and functional dendritic cells can be efficiently generated from umbilical cord blood-derived mononuclear cells by a simple two-step culture method," Transfusion 50: 2413-23, 2010.*

Van den Berk et al. "Cord blood mesenchymal stem cells propel human dendritic cells to an intermediate maturation state and boost interleukin-12 production by mature dendritic cells", Immunology 128: 564-72, 2009.*
Zaba et al. "Resident and "inflammatory" dendritic cells in human skin", Journal of Investigative Dermatology 129: 302-8, 2009.*
Riboldi et al. "Cutting Edge: Proangiogenic properties of alternatively activated dendritic cells", The Journal of Immunology 175: 2788-92, 2005.*
An International Search Report and a Written Opinion both dated Nov. 4, 2010, which issued during the prosecution of Applicant's PCT/IL2010/00558.
An International Preliminary Report on Patentability dated Sep. 4, 2012, which issued during the prosecution of Applicant's PCT/IL2010/00558.
Wallet M.A. (2005), "Immunoregulation of Dendritic Cells", Clinical Medicine & Research 3:166-175.
Cox K. (2005) "Plasmacytoid dendritic cells (PDC) are the major DC subset innately producing cytokines in human lymph nodes", J. Leukoc. Biol. 78:1142-1152.
Kim R. (2006), "Functional Role of Immature Dendritic Cells in Impaired Immunity and Solid Tumors and Their Targeted Strategies for Provoking Tumor Immunity", Clin. Exp. Immunol. 146:189-196.
McKenna K. (2005), "Plasmacytoid Dendritic Cells: linking Innate and Adaptive Immunity", J.Virol 79:17-27.
Dzionek A., (2000), "BDCA-2, BDCA-3, and BDCA-4: Three Markers for Distinct Subsets of Dendritic Cells in Human Peripheral Blood", J.Immunol. 165:6037-6046.
Kollet O. (2002), "Human CD34+CXCR4-sorted cells harbor intracellular CXCR4, which can be functionally expressed and provide NOD/SCID repopulation", Blood 100:2778-2786.
Kanamaru F. (2004), "Expression of membrane bound and soluble receptor activator of NFkappaB ligand (RANKL) in human T cells", Immunol Lett. 94:23946.
Stem Cell Information, (2007), "The Adult Stem Cell", The National Institute of Health, <http://stemcells.nih.gov/info/scireport/chapter4.asp>.
Badorff C. (2003), "Transdifferentiation of Blood-Derived Human Adult Endothelial Progenitor Cells into Functionally Active Cardiomyocytes", Circulation 107:1024-1032.
Nagasawa, T. (2008), "New niches for B cells", Nat Immunol 9:345.
Sapoznikov, A. (2008), "Perivascular clusters of dendritic cells provide critical survival signals to B cells in bone marrow niches", Nat Immunol 9:388.

(Continued)

*Primary Examiner* — Ruth Davis
*Assistant Examiner* — Emily Cordas
(74) *Attorney, Agent, or Firm* — Edwards Wildman Palmer LLP

(57) ABSTRACT

A method is provided, including obtaining a population of isolated immature antigen-presenting cells; enriching a population of isolated stem/progenitor cells within a larger population of cells; activating the population of immature antigen-presenting cells; and following the activating, inducing at least one process selected from the group consisting of: differentiation, expansion, activation, secretion of a molecule, and expression of a marker, by exposing the enriched stem/progenitor cell population to the population of activated antigen-presenting cells. Inducing the at least one process includes generating a lineage specific precursor/progenitor population (LSP) from the enriched stem/progenitor cell population. In addition, (1) obtaining the population of immature antigen-presenting cells includes obtaining the population of immature antigen-presenting cells from umbilical cord blood, and/or (2) enriching the population of stem/progenitor cells includes obtaining the population of stem/progenitor cells from umbilical cord blood. Other applications are also described.

11 Claims, 2 Drawing Sheets

(56) References Cited

OTHER PUBLICATIONS

Stier, S.(2005), "Osteopontin is a hematopoietic stem cell niche component that negatively regulates stem cell pool size", J Exp Med 201:1781.
Kohara, H. (2007), "Development of plasmacytoid dendritic cells in bone marrow stromal cell niches requires CXCL12-CXCR4 chemokine signaling", Blood 110:4153.
Dubois, B. (1998), "Critical role of IL-12 in dendritic cell-induced differentiation of naive B lymphocytes", J Immunol 161:2223.
Mahnke, K (2002), "Immature, but not inactive: the tolerogenic function of immature dendritic cells", Immunol Cell Biol 80:477.
Cheng, P. (2007), "Regulation of dendritic-cell differentiation by bone marrow stroma via different Notch ligands", Blood 109:507.
Tang, H. (2006), "Endothelial stroma programs hematopoietic stem cells to differentiate into regulatory dendritic cells through IL-10". Blood 108:1189.
Satthaphorn, S. (2001), "Dendritic cells (I): Biological functions", J R Coll Surg Edinb 46:9.
Romani, N. (1994), "Proliferating dendritic cell progenitors in human blood", J Exp Med 180:83.
Zhou, L. (1996), "CD14+ blood monocytes can differentiate into functionally mature CD83+ dendritic cells", Proc Natl Acad Sci U S A 93: 2588.
Watanabe, S. (2003), "The duration of signaling through CD40 directs biological ability of dendritic cells to induce antitumor immunity", J Immunol 171: 5828.
Sozzani, S. (2007), "Dendritic cell-endothelial cell cross-talk in angiogenesis", Trends Immunol 28:385.
Naldini, A. (2006), "Cutting edge: IL-1beta mediates the proangiogenic activity of osteopontin-activated human monocytes", J Immunol 177:4267.
Conejo-Garcia, J. R. (2004), "Tumor-infiltrating dendritic cell precursors recruited by a beta-defensin contribute to vasculogenesis under the influence of Vegf-A", Nat Med 10:950.
Butovsky, et al., Microglia activated by IL-4 or IFN-gamma differentially induce neurogenesis and oligodendrogenesis from adult stem/progenitor cells. Mol Cell Neurosci, Jan. 2006, vol. 31, No. 1, pp. 149-160.
Butovsky, et al., Microglia can be induced by IFN-gamma or IL-4 to express neural or dendritic-like markers. Mol Cell Neurosci, Jul. 2007, vol. 35, No. 3, pp. 490-500.
Rehman, et al., Peripheral blood "endothelial progenitor cells" are derived from monocyte/macrophages and secrete angiogenic growth factors. Circulation, Mar. 4, 2003, vol. 107, No. 8, pp. 1164-1169.
Aloisi, Immune Function of Microglia. Glia, Nov. 2001, vol. 36 No. 2, pp. 165-179.
Ferriero DM., "Neonatal Brain Injury", Review Article, pp. 1985-1995, 2004.
Perlman JM., "Brain Injury in the Term Infant", Seminars in Perinatology, pp. 415-424, 2004.
Grow J., "Pathogenesis of Hypoxic-ischemic cerebral injury in the Term infant: current concepts", Clinics in perinatology, pp. 585-602, 2002.
Silbereis JC, "Towards Improved animal models of neonatal white matter injury associated with cerebral palsy", Clinical Puzzle, pp. 678-688, 2010.
Pimentel-Coelho PM, "Cell-Therapy for Neonatal Hypoxic-ischemic Encephalopahty", Stem Cell and Development, pp. 299-310, 2010.
Alphonse RS, "Growth Factor, Stem Cells and Bronchpulmonary Dysplasia", Neonatology, pp. 326-337, 2011.
Tayman C., "Mesenchymal Stem Cell therapy in Necrotizing Enterocolitis: A Rut Study", Pediatric Research, vol. 70, No. 5, 2011.
Nankervis CA, The Neonatal intestinal Vasculature: Contributing Factors to Necrotizing Enterocolitis, Seminars in Perinatology, pp. 83-91, 2008.
Yael Porat et al. Isolation of an adult Blood-derived progenitor cell population capable of differention into angiogenic, mayocardial and neural lineages, Journal Compilation, 703-714, 2006.
Oswald et al., "Mesenchymal Stem Cell Can be differentiated into Endothelial Cells in Vitro", Stem Cells, 2004:22:377-384.
Yamada Y. et al., "Neuropilin-1 on hematopoietic cells as a source of vascular development", Blood, 2003, 101, 1801-1809.
ChenT., "Stromal Cells- Derived Factor 1/CXCR4 signaling modifieds the Capillary -Like Organization of Human Embryonic Stem Cell Derived Endothelium in Vitro", Stem Cells, 2007:25: 392-401.
Losordo and Dimmeler, "Therapeutic angiogenesis and Vasculogenesis for Ischemic Disease", Clinical Cardiology, 2692-2697, downloaded on Mar. 2012.
Rae et al., "Angiogenic potential of endothelial progenitor cells and embryonic Stem Cells", Vascular Cell, 2011, 3:11, 1-15.
Bagley et al, "Endothelial Precursor Cells as a Model of Tumor Endothelium: Characterization and Comparison with Mature Endothelial Cells", Cancer Researches, 63, 5866-5873, 2003.
James et al., "Expansion and maintenance of human embryonic stem cell derived endothelial cells by TGFB inhibition is Id1 Depented", NIH Public Access 1-14, 2010.
Highly efficient and feeder-free production [J Cell Physiol. 2008]—PubMed—NCBI.
Neumuller et al., "Immunological and ultrastructural characterization of endothelial cell cultures differentiated from human cord blood drived endothelial progenitor cells", Histochem Cell Biol, 126: 649-664, 2006.
Nadin et al., Phenotype and hematopoietic potential of side population cells throughout emryonic development, Blood, 2003 102:2436-2443.
Supplementary European Search Report for EP 10799518, dated Jul. 25, 2013, 8 pages.
Wang Q. et al; "Dendritic cells support hematopoiesis of bone marrow cells". Transplantation, Williams and Wilkins, Baltimore US, vol. 72, No. 5, Sep. 15, 2001, pp. 891-899, pp. 893-894.
Zia U.A. Mollah et al: "Cord Blood CD34+ Cells Differentiate into Dermal Dendritic Cells in Co-Culture with Cutaneous Fibroblasts or Stromal Cells", Journal of Investigative Dermatology, vol. 118, No. 3, Mar. 1, 2002, pp. 450-460.
J. Abbasian et al: "Allogeneic T cells induce rapid CD34+ cell differentiation into CD11c+CD86+ cells with direct and indirect antigen-presenting function", Blood, vol. 108, No. 1, Jul. 1, 2006, pp. 203-208.
Rondelli Damiano et al: "Rapid induction of CD40 on a subset of granulocyte colony-stimulating factor-mobilized CD34+ blood cells identifies myeloid committed progenitors and permits selection of nonimmunogenic CD40- progenitor cells", Blood, vol. 94, No. 7, Oct. 1, 1999, pp. 2293-2300.
Masatake Osawa et al: "Long-Term Lymphohematopoietic Reconstitution by a Single CD34-Low/Negative Hematopoietic Stem Cell", Science, vol. 273, Jul. 12, 1996, pp. 242-245.
Saito Yoshinobu et al: "Phagocytosis of co-developing neutrophil progenitors by dendritic cells in a culture of human CD34(+) cells with granulocyte colony-stimulating factor and tumor necrosis factor-alpha", International Journal of Hematology, vol. 88, No. 1, Jul. 2008, pp. 64-72, ISSN: 0925-5710.
M. Stec et al: "Expansion and differentiation of CD14+CD16 and CD14++CD16+ human monocyte subsets from cord blood CD34+hematopoietic progenitors", Journal of Leukocyte Biology, vol. 82, No. 3, Jun. 26, 2007, pp. 594-602, ISSN:0741-5400, DOI: 10.1189/jlb.0207117.
Berges C et al: "A cell line model for the differentiation of human dendritic cells", Biochemical and Biophysical Research Communications, Academic Press Inc. Orlando, FL, US, vol. 333, No. 3, Aug. 5, 2005, pp. 896-907, ISSN: 0006-291X, DOI: 10.1016/J.BBRC. 2005.05.171 [retrieved on Jun. 27, 2005].
An Office Action dated Mar. 24, 2014 which issued during the prosecution of Applicant's European App No. 10 799518.5.
Mikami et al.: "Implantation of Dendritic Cells in Injured Adult Spinal Cord Results in Activation of Endogenous Neural Stem/Progenitor Cells Leading to De Novo Neurogenesis and Functional Recovery" Journal of Neuroscience Research 76:453-465 (2004).
Porat et al.: "A novel potential therapy for vascular diseases: blood-derived stem/progenitor cells specifically activated by dendritic cells" Research Articl (2014).
An Office Action dated Apr. 24, 2014, which issued during the prosecution of U.S. Appl. No. 13/743,966.

* cited by examiner

METHOD FOR USING DIRECTING CELLS FOR SPECIFIC STEM/PROGENITOR CELL ACTIVATION AND DIFFERENTIATION

CROSS-REFERENCES TO RELATED APPLICATIONS

The present application claims the benefit of U.S. 61/588,228 to Porat et al., filed Jan. 19, 2012, entitled, "Method for using directing cells for specific stem/progenitor cell activation and differentiation."

The present application is related to U.S. patent application Ser. No. 13/004,751 to Porat (which published as US 2011/0143437), entitled, "Method for using directing cells for specific stem/progenitor cell activation and differentiation," filed Jan. 11, 2011, which is a continuation-in-part of and claims the priority of PCT/IL2010/000558 to Porat (which published as WO 2011/007348), entitled, "Method for using directing cells for specific stem/progenitor cell activation and differentiation," filed, Jul. 13, 2010, which claims priority from U.S. Provisional Patent Application 61/224,942 to Porat, entitled, "Method for using antigen-presenting cells and dendritic cells to direct stem/progenitor cell differentiation and activation," filed Jul. 13, 2009.

All of the above applications are incorporated herein by reference.

FIELD OF THE INVENTION

The present invention relates generally to stem cells. Specifically, the present invention relates to methods for regulating cell activation.

BACKGROUND

Based on their presentation of antigenic epitopes and secretion of various cytokines and chemokines which initiate and/or enhance many cell types, antigen-presenting cells (APC) and dendritic cells (DC) are known for their ability to alter and direct different immunological responses and thus induce a phenomenon of B and T cell plasticity. Similarly to multi-potential progenitor cells, APC and DC can be located in different tissues such as the lymph nodes and the bone marrow (BM) or in the circulation. Likewise, DC in different stages of maturity can be found in a variety of tissues.

Neurovascular injury is common in most prenatal, intrapartum, and postnatal cerebral pathologies. It is an important cause of fetal and neonatal morbidity and mortality, and of long term sequelae, e.g., cerebral palsy (CP) and mental retardation (MR) and epilepsy of both preterm and term born infants. In-utero hypoxic ischemic (HI) events (e.g., placental insufficiency, chronic fetal-to-maternal hemorrhage, stroke, infection and inflammation), perinatal events (e.g., placental abruption, respiratory failure) and neonatal disorders (e.g., chronic lung disease) are associated with acquired brain injuries that lead to CP. The potential use of stem cells from various sources to reduce neonatal brain damage being investigated in HI animal models shows improvement of sensorimotor functions and brain damage decrease.

In addition to brain damage, stem cells can be used to treat other intractable neonatal diseases such as Bronchopulmonary dysplasia (BPD) and necrotizing enterocolitis (NEC). BPD is a chronic lung disease, in preterm infants, caused by arrested alveolar growth and disrupted vasculogenesis that leads to chronic lung diseases. NEC is a condition, in premature infants, where portions of the bowel undergo necrosis due to intestinal ischemia resulting in death or long-term disability from gastrointestinal disease.

The following references may be of interest:

1. Ferriero D. M. (2004), "Neonatal brain injury". N Engl J. Med. 351:1985-1995.
2. Perlman J. M, (2004), "Brain injury in the term infant", Semin Perinatol 28:415-424.
3. Grow J. (2002), "Pathogenesis of hypoxic-ischemic cerebral injury in the term infant: current concepts", Clin Perinatol 29:585-602.
4. Silbereis J. C. (2010), "Towards improved animal models of neonatal white matter injury associated with cerebral palsy", Disease Models & Mechanisms 3:678-688.
5. Pimentel-Coelho P. M. (2010) "Cell therapy for neonatal hypoxic-ischemic encephalopathy", Stem Cells Dev. 19:299-310.
6. Alphonse R. S. (2011), "Growth Factors, Stem Cells and Bronchopulmonary Dysplasia", Neonatology 99:326-337
7. Tayman C. (2011), "Mesencchymal Stem Cell Therapy in Necrotizing Enterocolitis: A Rat Study", Pediatric Research 70:489-494.
8. Nankervis C. A. (2008), "The neonatal intestinal vasculature: contributing factors to necrotizing enterocolitis", Semin Perinatol. 32:83-91.
9. PCT Publication WO 08/140,316 to Meers
10. US Patent Application Publication 2008/0206286 to Yu
11. US Patent Application Publication 2008/0226612 to Treves et al
12. US Patent Application Publication 2008/0292601 to Song
13. US Patent Application Publication 2009/0131346 to Sorio
14. US Patent Application Publication 2010/0143311 to Mizukami et al
15. US Patent Application Publication 2009/0004157 to Kalinski
16. Wallet M. A. (2005), "Immunoregulation of Dendritic Cells", Clinical Medicine & Research 3:166-175
17. Cox K. (2005) "Plasmacytoid dendritic cells (PDC) are the major DC subset innately producing cytokines in human lymph nodes", J. Leukoc. Biol. 78:1142-1152
18. Kim R. (2006), "Functional Role of Immature Dendritic Cells in Impaired Immunity and Solid Tumors and Their Targeted Strategies for Provoking Tumor Immunity", Clin. Exp. Immunol. 146:189-196
19. McKenna K. (2005), "Plasmacytoid Dendritic Cells: linking Innate and Adaptive Immunity", J.Virol 79:17-27
20. Dzionek A., (2000), "BDCA-2, BDCA-3, and BDCA-4: Three Markers for Distinct Subsets of Dendritic Cells in Human Peripheral Blood", J.Immunol. 165:6037-6046
21. Stem Cell Information, (2007), "The Adult Stem Cell", The National Institute of Health
22. Kollet O. (2002), "Human CD34+CXCR4-sorted cells harbor intracellular CXCR4, which can be functionally expressed and provide NOD/SCID repopulation", Blood 100:2778-2786
23. Kanamaru F. (2004), "Expression of membrane bound and soluble receptor activator of NFkappaB ligand (RANKL) in human T cells", Immunol Lett. 94:23946
24. Badorff C. (2003), "Transdifferentiation of Blood-Derived Human Adult Endothelial Progenitor Cells into Functionally Active Cardiomyocytes", Circulation 107: 1024-1032
25. Nagasawa, T. (2008), "New niches for B cells", Nat Immunol 9:345
26. Sapoznikov, A. (2008), "Perivascular clusters of dendritic cells provide critical survival signals to B cells in bone marrow niches", Nat Immunol 9:388

27. Stier, S. (2005), "Osteopontin is a hematopoietic stem cell niche component that negatively regulates stem cell pool size", J Exp Med 201:1781
28. Kohara, H. (2007), "Development of plasmacytoid dendritic cells in bone marrow stromal cell niches requires CXCL12-CXCR4 chemokine signaling", Blood 110:4153
29. Cheng, P. (2007), "Regulation of dendritic-cell differentiation by bone marrow stroma via different Notch ligands", Blood 109:507
30. Dubois, B. (1998), "Critical role of IL-12 in dendritic cell-induced differentiation of naive B lymphocytes", J Immunol 161:2223
31. Mahnke, K. (2002), "Immature, but not inactive: the tolerogenic function of immature dendritic cells", Immunol Cell Biol 80:477
32. Tang, H. (2006), "Endothelial stroma programs hematopoietic stem cells to differentiate into regulatory dendritic cells through IL-10". Blood 108:1189
33. Satthaporn, S. (2001), "Dendritic cells (I): Biological functions", J R Coll Surg Edinb 46:9
34. Romani, N. (1994), "Proliferating dendritic cell progenitors in human blood", J Exp Med 180:83
35. Zhou, L. (1996), "CD14+ blood monocytes can differentiate into functionally mature CD83+ dendritic cells", Proc Natl Acad Sci USA 93: 2588
36. Watanabe, S. (2003), "The duration of signaling through CD40 directs biological ability of dendritic cells to induce antitumor immunity", J Immunol 171:5828
37. Sozzani, S. (2007), "Dendritic cell-endothelial cell crosstalk in angiogenesis", Trends Immunol 28:385
38. Naldini, A. (2006), "Cutting edge: IL-1beta mediates the proangiogenic activity of osteopontin-activated human monocytes", J Immunol 177:4267
39. Conejo-Garcia, J. R. (2004), "Tumor-infiltrating dendritic cell precursors recruited by a beta-defensin contribute to vasculogenesis under the influence of Vegf-A", Nat Med 10:950
40. U.S. Pat. No. 5,969,105 (1999) to Feng Y et al. (1997), Stem cell factor agonists. application Ser. No. 08/955,848
41. US Patent Application Publication 2007/0269867 (2007) to Ghosh S K et al. (2004), Protein markers associated with bone marrow stem cell differentiation into early progenitor dendritic cells.
42. U.S. Pat. No. 6,479,286 (2002) to Nelson E L et al. (1999) Methods and compositions for making dendritic cells from expanded populations of monocytes and for activating T cells.
43. PCT Publication WO 98/053048 to Nelson et al.
44. U.S. Pat. No. 7,030,228 (2006) to Schmitz et al. (2000) Antigen-binding fragments specific for dendritic cells, compositions and methods of use thereof antigens recognized thereby and cells obtained thereby.
45. US 2011/0143437 Porat, entitled, "Method for using directing cells for specific stem/progenitor cell activation and differentiation," filed Jan. 11, 2011.

SUMMARY OF THE INVENTION

Under normal conditions, antigen-presenting cells (APC) and especially dendritic cells (DC) are used for the activation, direction and alteration of the immune system response. For some applications of the present invention, methods for using APC and especially DC are used to direct activation and/or effect differentiation of tissue-derived cells (TDC). In the context of this application, in the specification and in the claims, "tissue-derived cells (TDC)" means a population containing stem/progenitor cells and other cells such as mature cells, the TDC having been derived from an original population of cells in a tissue by (a) isolating at least a first sub-population of the population from a second sub-population of the population, and (b) increasing the proportion of stem/progenitor cells in the first sub-population of cells. As described herein, this selected population of TDC is typically acted on by antigen-presenting cells, specifically dendritic cells. APC, typically dendritic cells, are examples of a directing cell population (DCP) (defined below), and are used in the activation, direction and alteration of TDC, e.g., multipotent adult stem/progenitor cells (MASPC), effector cells prior to their terminal differentiation, and embryonic stem cells. As a result, a specific population of cells (e.g., lineage specific precursor/progenitors (LSP)), soluble molecules thereof are generated which can be effective in tissue regeneration, cancer immunity, inhibition of autoimmunity disorders and chronic inflammation, enhancement of cell engraftment, and homeostasis.

By way of definition, a "directing cell population (DCP)" is a population of cells comprising antigen-presenting cells (APC) and/or dendritic cells (DC) that are cultured under specific conditions. The DCP is typically used to direct the activation and/or expansion and/or differentiation of cells.

It is to be noted that the DCP and/or the TDC may be isolated from extracted blood (e.g., peripheral blood) of a patient or from umbilical cord blood.

Disclosed herein are methods to culture, enrich, and use a DCP in order to be cultured together with TDC (e.g., an MASPC-rich population, and/or subpopulations thereof). Such co-culturing of the DCP with the TDC induces the activation, and/or proliferation, and/or expansion, and/or differentiation, and/or induction of biochemical activity, etc., of the TDC as a therapeutic, diagnostic, and research tools. For some applications, the co-culturing of the DCP with the TDC induces the activation and/or proliferation, and/or expansion, and/or differentiation, and/or induction of biochemical activity, etc., of the DCP for therapeutic, diagnostic, and research tools. Typically, the product of the co-culture between the DCP and the TDC is enriched. For some applications, a subpopulation of the co-culture is enriched and/or purified at any stage of the co-culture procedure, e.g., at the end of the co-culture. Additionally, for some applications, these subpopulations may be administered to a patient and/or stored in a bank for future use.

"Expansion," in the context of this application, in the specification and in the claims, means increasing the proportion of a given cell type with respect to other cell types, within a larger population of cells, e.g., in culture. The increase in the proportion of the given cell type with respect to other cell types, results from either (a) proliferation of the cell type or (b) death of other cell types in the larger population, (c) differentiation and de-differentiation of the cell type or any of the other cell types in the population, or (d) a combination of any of (a), (b), and/or (c).

As shown in the experimental data presented herein, TDC are a cell population that can undergo differentiation into an LSP when acted upon by the DCP. For example, a TDC of enriched MASPC is shown to differentiate into an LSP of endothelial progenitor cells (EPC). Additionally, as shown in the experimental data presented herein, TDC, e.g., containing enriched MASPC, can also undergo expansion in culture, thus yielding a population of cells with an increased proportion of MASPC, which can further differentiate into an LSP. Ultimately, for some applications, the LSP contains a population of precursor and/or mature cells of a given lineage and includes a subpopulation comprising MASPC. For other applications, the LSP contains a population of precursor and/ or mature cells of a given lineage and does not include a subpopulation comprising MASPC.

One example of such an LSP that is described herein and shown in the experimental data, is a lineage-specific population which contains a population of cells which demonstrate increased cytotoxic activity toward cancer cells. TDC, including MASPC and effector cells such as T cells and/or natural killer cell, are activated by the DCP to produce a lineage-specific, anti-cancer cell progenitor population (LSP-aCCP). The LSP-aCCP contain a population of mature activated effector cells as well as a population of precursor cells that are directed to eventually differentiate into mature activated effector cells. In such a manner, the LSP-aCCP contain cells that are available for immediate anti-cancer use (LSP containing activated effect cells) as well as a sub-population of latent cells (LSP containing MASPC) which can replenish the mature activated effector cells by differentiating into the mature activated effector cells at a later stage.

There is therefore provided, in accordance with an application of the present invention, a method, including:
obtaining a population of isolated immature antigen-presenting cells;
enriching a population of isolated stem/progenitor cells within a larger population of cells;
activating the population of immature antigen-presenting cells; and
following the activating, inducing at least one process selected from the group consisting of: differentiation, expansion, activation, secretion of a molecule, and expression of a marker, by exposing the enriched stem/progenitor cell population to the population of activated antigen-presenting cells,
wherein inducing the at least one process includes generating a lineage specific precursor/progenitor population (LSP) from the enriched stem/progenitor cell population, and:
(1) wherein obtaining the population of immature antigen-presenting cells includes obtaining the population of immature antigen-presenting cells from umbilical cord blood, or
(2) wherein enriching the population of stem/progenitor cells includes obtaining the population of stem/progenitor cells from umbilical cord blood.

For some applications:
(1) obtaining the population of immature antigen-presenting cells includes obtaining the population of immature antigen-presenting cells from umbilical cord blood, and
(2) enriching the population of stem/progenitor cells includes obtaining the population of stem/progenitor cells from umbilical cord blood.

For some applications:
(1) obtaining the population of immature antigen-presenting cells includes obtaining the population of immature antigen-presenting cells from an umbilical cord blood sample, and
(2) enriching the population of stem/progenitor cells includes obtaining the population of stem/progenitor cells from the same umbilical cord blood sample.

For some applications, obtaining the population of immature antigen-presenting cells includes obtaining the population of immature antigen-presenting cells from umbilical cord blood.

For some applications, enriching the population of stem/progenitor cells includes obtaining the population of stem/progenitor cells from umbilical cord blood.

For some applications, the at least one process includes inducing expression of the marker, and inducing the expression includes at least one step selected from the group consisting of: (a) increasing the expression of the marker from a state of no expression of the marker to a positive level of expression, and (b) increasing the expression of the marker from a low, positive level of expression of the marker to a higher level of expression of the marker.

For some applications, the at least one process includes inducing secretion of the molecule, and wherein inducing the secretion includes at least one step selected from the group consisting of: (a) increasing the secretion of the molecule from a state of no secretion of the molecule to a positive level of secretion, and (b) increasing the secretion of the molecule from a low, positive level of secretion of the molecule to a higher level of secretion of the molecule.

There is further provided, in accordance with an application of the present invention,
receiving the lineage specific precursor/progenitor population described hereinabove; and
administering to a patient one or more compositions selected from the group consisting of: the lineage specific precursor/progenitor population and a soluble component of the lineage specific precursor/progenitor population.

For some applications, the method further includes identifying the patient as having reduced blood flow in a portion of a body of the patient,
administering includes administering the one or more compositions in response to the identifying, and
administering includes increasing blood flow of the patient.

For some applications, the population of immature antigen-presenting cells includes immature dendritic cells, and wherein obtaining the population of antigen-presenting cells includes obtaining the population of antigen-presenting cells including the immature dendritic cells, and wherein inducing the at least one process includes inducing the at least one process using the population of activated antigen-presenting cells.

For some applications, inducing the at least one process includes inducing the expression of the marker, and inducing the expression of the marker includes increasing a proportion of cells in the LSP that have at least one characteristic selected from the group consisting of: expression of CD34, expression of CD184, and co-expression of CD34 and CD184.

For some applications, inducing the expression of the marker includes increasing the proportion of cells in the LSP, that co-express CD34 and CD184, to at least 2.5%.

For some applications, generating the lineage specific precursor/progenitor population includes generating a predetermined lineage specific precursor/progenitor cell population, and wherein inducing the at least one process includes generating a population of at least 1 million lineage specific precursor/progenitor cells, wherein:
at least 2.5% of the LSP cell population express one or more markers selected from the group consisting of: CD31, CD133, CD144, CD202b, von Willebrand factor (vWF), CD102, CD105, CD106, CD109, CD114, CDw145, CD201, CD299, and CD309,
at least some of the at least 2.5% of the cells of the population co-express CD309 and CD202b,
at least some of the at least 2.5% of the cells of the population co-express CD31 and VEGFR1,
at least some of the at least 2.5% of the cells of the population uptake Ac-LDL and express Ulex lectin,
at least 2.5% of the LSP cell population express one or more markers selected from the group consisting of: CD7, CD31, CD33, CD34, CD90, CD105, CD115, CD117, CDw123, CD124, CD157, CD164, CD172a, CD173, CD175, CD178, CD184, CD191, CD202b, CD292, and Stro-1, at least some of the at least 2.5% of the cells of the population express CD34 and CD184, and the LSP cell population secretes one or more molecules selected from the group consisting of: G-CSF, SDF-1/CXCR4, IL-8, IL-10, IFN alpha (IFNα), IFN beta (IFNβ), IFN gamma (IFNγ), TGF beta (TGFβ), basic FGF (b-FGF), IL-12, IL-18 and IL-27.

For some applications:

activating the population of immature antigen-presenting cells includes:

increasing, to at least 15%, a proportion of the antigen-presenting cells in a greater population of cells that includes the antigen-presenting cells; and prior to the step of exposing the enriched population of stem/progenitor cells to the population of antigen-presenting cells, facilitating the activation of the immature antigen-presenting cells by performing at least one action selected from the group consisting of: providing activation signals to the antigen-presenting cells, and incubating the antigen-presenting cells for a period of 0.5 hours to 3 days, and wherein immediately upon the step of exposing the enriched population of stem/progenitor cells to the population of antigen-presenting cells, the antigen-presenting cells are a sub-population of a larger population that also includes the enriched population of stem/progenitor cells, the antigen-presenting cells being 2-20% of the larger population, prior to any incubation of the larger population.

For some applications, increasing the antigen-presenting cells to the proportion of at least 15% of the greater population includes at least one action selected from the group consisting of:

(a) increasing a proportion of cells expressing CD141 to at least 1% of the greater population, and (b) increasing, to at least 5% of the greater population, expression of a marker selected from the group consisting of: CD303 and CD304.

For some applications, facilitating includes performing the step of facilitating subsequently to increasing the antigen-presenting cells to the proportion of at least 15% of the greater population.

For some applications, incubating includes incubating the antigen-presenting cells for a period of 0.5 hours to 22 hours.

For some applications, facilitating includes incubating the antigen-presenting cells in a medium including at least one component selected from the group consisting of: IL-10, IL-12, IL-18, IL-27, TGF beta, bFGF, and VEGF.

For some applications, facilitating includes incubating the antigen-presenting cells in a medium including at least one component selected from the group consisting of: IL-10 and VEGF.

For some applications, facilitating includes incubating the antigen-presenting cells in a medium including at least one component selected from the group consisting of: IL-10, IL-12, IL-18, IL-27, TGF beta, bFGF, and VEGF, and wherein inducing the at least one process includes increasing a proportion of the antigen-presenting cells expressing increased intensity of CD141 to at least 1% of the greater population.

For some applications, the method further includes freezing the greater population.

For some applications, facilitating includes incubating the antigen-presenting cells in a medium including at least one component selected from the group consisting of: IL-10, TGF beta, bFGF, and VEGF, and wherein inducing the at least one process includes increasing, to at least 5% of the lineage specific precursor/progenitor population, a proportion of cells that have at least one characteristic selected from the group consisting of: uptake of AC-LDL combined with expression of Ulex lectin, expression of CD31, expression of CD133, expression of CD144, expression of CD202b, expression of VEGR1, expression of von Willebrand factor (vWF), expression of CD102, expression of CD105, expression of CD106, expression of CD109, expression of CD114, expression of CDw145, expression of CD201, expression of CD299, expression of CD309, VEGFR1, co-expression of CD202b and CD31, and co-expression of CD184 and CD34.

For some applications, obtaining the antigen-presenting cells includes obtaining a population of at least 1 million antigen-presenting cells, and wherein at least 5% of the antigen-presenting cells express one or more markers selected from the group consisting of: CD1c, CD1b, CD1e, CD11c, CD40, CD49d, CD53, CD68, CD74, CD80, CD83, CD85, CD86, CDw123, CD172b, CD180, CD141, CD206, CD208, CD209, CD218, CD258, CD301, CD303, and CD304.

For some applications, at least 5% of the antigen-presenting cells express one or more markers selected from the group consisting of: CD1c, CD80, CD83, CD86, CD141, CD303, and CD304.

For some applications, exposing the enriched stem/progenitor cell population to the population of activated antigen-presenting cells includes, prior to inducing the at least one process, generating a heterogeneous population of cells, and wherein:

the population of antigen-presenting cells is at least 2% of the cells in the heterogeneous population, the population of enriched stem/progenitor cells is at least 1% of the cells in the heterogeneous population of cells, and the at least 1% of the cells in the heterogeneous population of cells express one or more markers selected from the group consisting of: CD33, CD31, CD34, CD90, CD184, and CD202b.

For some applications, generating the heterogeneous population includes generating a heterogeneous population, wherein:

the at least 5% of the antigen-presenting cells express one or more markers selected from the group consisting of: CD1c, CD86, CD141, CD303, and CD304, and the at least 1% of the cells in the heterogeneous population of cells expressing the one or more markers express one or more markers selected from the group consisting of: CD31, CD34, and CD184.

For some applications, inducing the at least one process includes generating a population of at least 2 million lineage specific precursor/progenitor cells, wherein:

a first subset of the population of at least 2 million lineage specific precursor/progenitor cells includes at least 5% of the at least 2 million cells, and expresses one or more markers selected from the group consisting of: CD1c, CD1b, CD1e, CD11c, CD40, CD49d, CD53, CD68, CD74, CD80, CD83, CD85, CD86, CDw123, CD172b, CD180, CD141, CD206, CD208, CD209, CD218, CD258, CD301, CD303 and CD304, a second subset of the population of at least 2 million lineage specific precursor/progenitor cells includes at least 2.5% of the at least 2 million cells, and expresses one or more markers selected from the group consisting of: CD7, CD31, CD33, CD34, CD90, CD105, CD115, CD117, CD124, CD157, CD164, CD172a, CD173, CD175, CD178, CD184, CD191, CD202b, CD292, CD309, VEGFR1, and Stro-1, and a plurality of cells in the population of at least 2 million lineage specific precursor/progenitor cells secrete one or more molecules selected from the group consisting of: G-CSF, SDF-1/CXCR4, IL-8, IL-10, IFN alpha (IFNα), IFN beta (IFNβ), IFN gamma (IFNγ), TGF beta (TGFβ), basic FGF (b-FGF), IL-12, IL-18 and IL-27.

For some applications, generating the population of at least 2 million lineage specific precursor/progenitor cells includes generating a population in which a portion of cells of the second subset express CD309 and CD202b.

For some applications, generating the population of at least 2 million lineage specific precursor/progenitor cells includes generating a population in which a portion of cells of the second subset express CD31 and VEGFR1.

For some applications, generating the population of at least 2 million lineage specific precursor/progenitor cells includes generating a population in which a portion of cells of the second subset uptakes Ac-LDL and expresses Ulex lectin.

For some applications, generating the population of at least 2 million lineage specific precursor/progenitor cells includes generating a population in which:

the first subset expresses one or more markers selected from the group consisting of: CD141, CD86, CD303, and CD304, and the second subset expresses one or more markers express one or more markers selected from the group: CD34 and CD184.

For some applications, inducing the at least one process includes generating a population of at least 1 million lineage specific precursor/progenitor cells, wherein:

a first subset of the population of at least 1 million lineage specific precursor/progenitor cells includes at least 10% of the at least 1 million cells, and expresses one or more markers selected from the group consisting of: CD1c, CD141, CD303, CD304, and CD86, a second subset of the population of at least 1 million lineage specific precursor/progenitor cells includes at least 10% of the at least 1 million cells, and expresses one or more markers selected from the group consisting of: CD34, CD184, CD31, and CD202b, a third subset of the population of at least 1 million lineage specific precursor/progenitor cells includes at least 2.5% of the at least 1 million cells, and expresses CD309 and CD202b, at least some cells of the population of at least 1 million lineage specific precursor/progenitor cells include at least 5% of the at least 1 million cells, and express CD31 and VEGFR1, and at least some cells of the population of at least 1 million lineage specific precursor/progenitor cells uptake Ac-LDL and express Ulex lectin.

For some applications:

obtaining the population of immature antigen-presenting cells includes:

freezing at least 100 million mononuclear cells;
thawing the frozen cells; and
obtaining the population of immature antigen-presenting cells from the thawed cells, wherein enriching the population of stem/progenitor cells includes obtaining the population of stem/progenitor cells from the thawed cells.

There is further provided, in accordance with an application of the present invention, a composition of matter, including a population of at least 1 million isolated lineage specific precursor/progenitor cells, wherein a first subset of the population includes 2.5-25% of the at least 1 million cells, and expresses CD304, wherein a second subset of the population includes 2.5-15% of the at least 1 million cells, and co-expresses CD34 and CD184, and wherein a third subset of the population includes:

(a) 13-53% of the at least 1 million cells, which co-express CD31 and VEGFR1, (b) 0.5-15% of the at least 1 million cells, which co-express CD202b and CD309, and (c) 5-35% of the at least 1 million cells, which co-expresses Ulex lectin and uptake of Ac-LDL.

For some applications, the composition of matter is frozen.

For some applications, a soluble component of the composition of matter is configured to be administered to a patient.

For some applications, the population includes at least 10 million isolated lineage specific precursor/progenitor cells.

For some applications, the composition of matter is configured to increase blood flow in a portion of a body of the patient, and wherein the patient has reduced blood flow.

There is therefore provided, in accordance with an embodiment of the present invention, a method, including:

obtaining a population of immature antigen-presenting cells;

enriching a population of stem/progenitor cells within a larger population of cells;

activating the population of immature antigen-presenting cells; and following the activating, inducing at least one process selected from the group consisting of: differentiation, expansion, activation, secretion of a molecule, and expression of a marker, by exposing the enriched stem/progenitor cell population to the population of activated antigen-presenting cells, wherein inducing the at least one process includes generating a lineage specific precursor/progenitor population (LSP) from the enriched stem/progenitor cell population.

In some applications of the present invention, obtaining the population of immature antigen-presenting cells includes obtaining the population of immature antigen-presenting cells from umbilical cord blood.

In some applications of the present invention, enriching the population of stem/progenitor cells includes obtaining the population of stem/progenitor cells from umbilical cord blood.

For some applications, the at least one process includes inducing expression of the marker, and inducing the expression includes at least one step selected from the group consisting of: (a) increasing the expression of the marker from a state of no expression of the marker to a positive level of expression, and (b) increasing the expression of the marker from a low, positive level of expression of the marker to a higher level of expression of the marker.

For some applications, the at least one process includes inducing secretion of the molecule, and inducing the secretion includes at least one step selected from the group consisting of: (a) increasing the secretion of the molecule from a state of no secretion of the molecule to a positive level of secretion, and (b) increasing the secretion of the molecule from a low, positive level of secretion of the molecule to a higher level of secretion of the molecule.

For some applications, the step of exposing the enriched stem/progenitor cell population to the population of activated antigen-presenting cells is performed in a common culture medium, and wherein the method does not include adding cytokines to the common culture medium.

There is also provided, in accordance with an application of the present invention, receiving the lineage specific precursor/progenitor population; and administering to a patient one or more compositions selected from the group consisting of: the lineage specific precursor/progenitor population and a soluble component of the lineage specific precursor/progenitor population.

For some applications, the method further includes identifying the patient as having reduced blood flow in a portion of a body of the patient,
wherein administering includes administering the one or more compositions in response to the identifying, and
wherein administering includes increasing blood flow of the patient.

For some applications, the population of immature antigen-presenting cells includes immature dendritic cells, and obtaining the population of antigen-presenting cells includes obtaining the population of antigen-presenting cells including the immature dendritic cells, and inducing the at least one process includes inducing the at least one process using the population of activated antigen-presenting cells.

For some applications, inducing the at least one process includes inducing the expression of the marker, and inducing the expression of the marker includes increasing a proportion of cells in the LSP that have at least one characteristic selected from the group consisting of: expression of CD34, expression of CD184, and co-expression of CD34 and CD184.

For some applications, inducing the expression of the marker includes increasing the proportion of cells in the LSP, that co-express CD34 and CD184, to at least 2.5%.

For some applications, increasing the proportion of cells that co-express CD34 and CD184 includes increasing the proportion to 2.5-70%.

For some applications, inducing the expression of the marker includes causing some of the cells in the LSP to co-express CD31 and CD202b, and causing some of the cells to co-express CD31 and CD202b includes causing at least 2% of the cells in the LSP to co-express CD31 and CD202b.

For some applications, causing some of the cells in the LSP to co-express CD31 and CD202b includes causing 2-70% of the cells in the LSP to co-express CD31 and CD202b.

For some applications, generating the lineage specific precursor/progenitor population includes generating a predetermined lineage specific precursor/progenitor cell population, and inducing the at least one process includes generating a population of at least 1 million lineage specific precursor/progenitor cells, wherein:
at least 2.5% of the LSP cell population express one or more markers selected from the group consisting of: CD31, CD133, CD144, CD202b, von Willebrand factor (vWF), CD102, CD105, CD106, CD109, CD114, CDw145, CD201, CD299, and CD309,
at least some of the at least 2.5% of the cells of the population co-express CD309 and CD202b,
at least some of the at least 2.5% of the cells of the population co-express CD31 and VEGFR1,
at least some of the at least 2.5% of the cells of the population uptake Ac-LDL and express Ulex lectin,
at least 2.5% of the LSP cell population express one or more markers selected from the group consisting of: CD7, CD31, CD33, CD34, CD90, CD105, CD115, CD117, CDw123, CD124, CD157, CD164, CD172a, CD173, CD175, CD178, CD184, CD191, CD202b, CD292, and Stro-1,
at least some of the at least 2.5% of the cells of the population co-express CD31 and CD202b,
at least some of the at least 2.5% of the cells of the population express CD34 and CD184, and
the LSP cell population secretes one or more molecules selected from the group consisting of: G-CSF, SDF-1/CXCR4, IL-8, IL-10, IFN alpha (IFNα), IFN beta (IFNβ), IFN gamma (IFNγ), TGF beta (TGFβ), basic FGF (b-FGF), IL-12, IL-18 and IL-27.

For some applications, increasing the proportion of cells that co-express CD309 and CD202b includes increasing the proportion co-expressing CD309 and CD202b to 2.5-70%.

For some applications, increasing the proportion of cells that co-express CD31 and VEGFR1 includes increasing the proportion of cells co-expressing CD31 and VEGFR1 to 2.5-70%.

For some applications:
activating the population of immature antigen-presenting cells includes:
increasing, to at least 15%, a proportion of the antigen-presenting cells in a greater population of cells that includes the antigen-presenting cells; and
prior to the step of exposing the enriched population of stem/progenitor cells to the population of antigen-presenting cells, facilitating the activation of the immature antigen-presenting cells by performing at least one action selected from the group consisting of: providing activation signals to the antigen-presenting cells, and incubating the antigen-presenting cells for a period of 0.5 hours to 3 days, and
immediately upon the step of exposing the enriched population of stem/progenitor cells to the population of antigen-presenting cells, the antigen-presenting cells are a sub-population of a larger population that also includes the enriched population of stem/progenitor cells, the antigen-presenting cells being 2-20% of the larger population, prior to any incubation of the larger population.

For some applications, increasing the antigen-presenting cells to the proportion of at least 15% of the greater population includes at least one action selected from the group consisting of:
(a) increasing a proportion of cells expressing CD141 to at least 1% (e.g., at least 5%) of the greater population,
(b) increasing, to at least 5% of the greater population, expression of a marker selected from the group consisting of: CD303 and CD304, and
(c) increasing a proportion of cells expressing CD86 to at least 5% of the greater population.

For some applications, facilitating includes performing the step of facilitating subsequently to increasing the antigen-presenting cells to the proportion of at least 15% of the greater population.

For some applications, incubating includes incubating the antigen-presenting cells for a period of 0.5 hours to 22 hours.

For some applications, facilitating includes incubating the antigen-presenting cells in a medium including at least one component selected from the group consisting of: IL-10, IL-12, IL-18, IL-27, TGF beta, bFGF, and VEGF.

For some applications, facilitating includes incubating the antigen-presenting cells in a medium including at least one component selected from the group consisting of: IL-10, IL-12, IL-18, IL-27, TGF beta, bFGF, and VEGF, and inducing the at least one process includes increasing a proportion of the antigen-presenting cells expressing increased intensity of CD141 to at least 1% (e.g., 2.5-50%) of the greater population.

In some applications of the present invention, the method further includes freezing the greater population.

For some applications, facilitating includes incubating the antigen-presenting cells in a medium including at least one component selected from the group consisting of: IL-10, TGF beta, bFGF, and VEGF, and wherein inducing the at least one process includes increasing, to at least 5% of the lineage specific precursor/progenitor population, a proportion of cells that have at least one characteristic selected from the group consisting of: uptake of AC-LDL combined with expression of Ulex lectin, expression of CD31, expression of CD133, expression of CD144, expression of CD202b, expression of VEGR1, expression of von Willebrand factor (vWF), expression of CD102, expression of CD105, expression of CD106, expression of CD109, expression of CD114, expression of CDw145, expression of CD201, expression of CD299, expression of CD309, VEGFR1, co-expression of CD202b and CD31, and co-expression of CD184 and CD34.

For some applications, the method includes:
enriching a population of immune effector cells;
following the activating of the population of antigen-presenting cells, activating the effector cells by co-culturing the antigen-presenting cells and the effector cells in a co-culture; and
adding to the co-culture the enriched population of stem/progenitor cells,
wherein exposing the enriched stem/progenitor cell population to the population of antigen-presenting cells includes exposing the co-culture of the antigen-presenting cells and the effector cells to the enriched stem/progenitor cell population, and
wherein inducing the at least one process includes, responsively to the exposing, creating a lineage-specific precursor/progenitor population.

For some applications, creating the lineage-specific precursor/progenitor population includes creating a lineage-specific precursor/progenitor population having a percentage increase of cytotoxic activity of at least 150%, versus cultured peripheral blood mononuclear cells.

There is also provided, in accordance with an application of the present invention, a method including:
receiving the lineage specific precursor/progenitor population; and
administering to a patient one or more compositions selected from the group consisting of: the lineage specific precursor/progenitor population and a soluble component of the lineage specific precursor/progenitor population.

For some applications:
creating the lineage-specific precursor/progenitor population includes creating a lineage-specific precursor/progenitor population having at least 10% of cells in the lineage-specific precursor/progenitor population which express one or more markers selected from the group consisting of: CD86, CD3, CD8, CD4, and CD56,
at least 10% of the cells in the lineage-specific precursor/progenitor population co-express CD34 and CD184, and
at least 10% of the cells in the lineage-specific precursor/progenitor population express one or more markers selected from the group consisting of CD86 and CD141.

For some applications, for at least eight days following the activation:
at least 10% of cells in the population express one or more markers selected from the group consisting of: CD86, CD3, CD8, CD4, and CD56,
at least 10% of the cells in the lineage-specific precursor/progenitor population co-express CD34 and CD184, and
at least 10% of the cells in the lineage-specific precursor/progenitor population express one or more markers selected from the group consisting of CD86 and CD141.

For some applications, obtaining the antigen-presenting cells includes obtaining a population of at least 1 million antigen-presenting cells, and at least 5% of the antigen-presenting cells express one or more markers selected from the group consisting of: CD1c, CD1b, CD1e, CD11c, CD40, CD49d, CD53, CD68, CD74, CD80, CD83, CD85, CD86, CDw123, CD172b, CD180, CD141, CD206, CD208, CD209, CD218, CD258, CD301, CD303, and CD304.

For some applications, at least 5% of the antigen-presenting cells express one or more markers selected from the group consisting of: CD1c, CD80, CD83, CD86, CD141, CD303, and CD304.

For some applications, exposing the enriched stem/progenitor cell population to the population of activated antigen-presenting cells includes, prior to inducing the at least one process, generating a heterogeneous population of cells, and:
the population of antigen-presenting cells is at least 2% of the cells in the heterogeneous population,
the population of enriched stem/progenitor cells is at least 1% of the cells in the heterogeneous population of cells, and
the at least 1% of the cells in the heterogeneous population of cells express one or more markers selected from the group consisting of: CD33, CD31, CD34, CD90, CD184, and CD202b.

For some applications, generating the heterogeneous population includes generating a heterogeneous population, wherein:
the at least 5% of the antigen-presenting cells express one or more markers selected from the group consisting of: CD1c, CD86, CD141, CD303, and CD304, and
the at least 1% of the cells in the heterogeneous population of cells expressing the one or more markers express one or more markers selected from the group consisting of: CD31, CD34, and CD184.

For some applications, generating the heterogeneous population includes generating a heterogeneous population, wherein:
the at least 5% of the antigen-presenting cells express at least one marker selected from the group consisting of: CD141, CD303, CD304, and CD86.

For some applications, inducing the at least one process includes generating a population of at least 2 million lineage specific precursor/progenitor cells, wherein:
a first subset of the population of at least 2 million lineage specific precursor/progenitor cells includes at least 5% of the at least 2 million cells, and expresses one or more markers selected from the group consisting of: CD1c, CD1b, CD1e, CD11c, CD40, CD49d, CD53, CD68, CD74, CD80, CD83, CD85, CD86, CDw123, CD172b, CD180, CD141, CD206, CD208, CD209, CD218, CD258, CD301, CD303 and CD304,
a second subset of the population of at least 2 million lineage specific precursor/progenitor cells includes at least 2.5% of the at least 2 million cells, and expresses one or more markers selected from the group consisting of: CD7, CD31, CD33, CD34, CD90, CD105, CD115, CD117, CD124, CD157, CD164, CD172a, CD173, CD175, CD178, CD184, CD191, CD202b, CD292, CD309, VEGFR1, and Stro-1, and
a plurality of cells in the population of at least 2 million lineage specific precursor/progenitor cells secrete one or more molecules selected from the group consisting of: G-CSF, SDF-1/CXCR4, IL-8, IL-10, IFN alpha (IFNα), IFN beta (IFNβ), IFN gamma (IFNγ), TGF beta (TGFβ), basic FGF (b-FGF), IL-12, IL-18 and IL-27.

For some applications, generating the population of at least 2 million lineage specific precursor/progenitor cells includes generating a population in which a portion of cells of the second subset express CD309 and CD202b.

For some applications, generating the population of at least 2 million lineage specific precursor/progenitor cells includes generating a population in which a portion of cells of the second subset express CD31 and VEGFR1.

For some applications, generating the population of at least 2 million lineage specific precursor/progenitor cells includes generating a population in which a portion of cells of the second subset uptakes Ac-LDL and expresses Ulex lectin.

For some applications, generating the population of at least 2 million lineage specific precursor/progenitor cells includes generating a population in which:
the first subset expresses one or more markers selected from the group consisting of: CD141, CD86, CD303, and CD304, and
the second subset expresses one or more markers express one or more markers selected from the group: CD34 and CD184.

For some applications, inducing the at least one process includes generating a population of at least 1 million lineage specific precursor/progenitor cells, wherein:
a first subset of the population of at least 1 million lineage specific precursor/progenitor cells includes at least 10% of the at least 1 million cells, and expresses one or more markers selected from the group consisting of: CD1c, CD141, CD303, CD304, and CD86,
a second subset of the population of at least 1 million lineage specific precursor/progenitor cells includes at least 10% of the at least 1 million cells, and expresses one or more markers selected from the group consisting of: CD34, CD184, CD31, and CD202b,
a third subset of the population of at least 1 million lineage specific precursor/progenitor cells includes at least 2.5% of the at least 1 million cells, and expresses CD309 and CD202b,
at least some cells of the population of at least 1 million lineage specific precursor/progenitor cells include at least 5% of the at least 1 million cells, and express CD31 and VEGFR1, and
at least some cells of the population of at least 1 million lineage specific precursor/progenitor cells uptake Ac-LDL and express Ulex lectin.

For some applications:
obtaining the population of immature antigen-presenting cells includes:
freezing at least 100 million mononuclear cells;
thawing the frozen cells; and
obtaining the population of immature antigen-presenting cells from the thawed cells, and
enriching the population of stem/progenitor cells includes obtaining the population of stem/progenitor cells from the thawed cells.

There is also provided, in accordance with an application of the present invention, a composition of matter, including a heterogeneous population of cells, the heterogeneous population of cells including:
(a) a population of at least 1 million antigen-presenting cells; and
(b) a population of enriched stem/progenitor cells,
wherein the population of antigen-presenting cells is at least 2.5% of the cells in the heterogeneous population,
wherein at least 5% of the antigen-presenting cells express one or more markers selected from the group consisting of: CD1c, CD80, CD83, CD86, CD141, CD218, CD301, CD303, and CD304,
wherein the population of enriched stem/progenitor cells is at least 1% of the cells in the heterogeneous population of cells, and
wherein at least 1% of the cells in the heterogeneous population of cells express one or more markers selected from the group consisting of: CD33, CD31, CD34, CD90, CD184, and CD202b.

For some applications:
the population of antigen-presenting cells is at least 2.5-20% of the cells in the heterogeneous population,
the at least 5% of the antigen-presenting cells express one or more markers selected from the group consisting of: CD1c, CD86, CD141, CD303, and CD304,
2.5-50% of the cells in the heterogeneous population of cells express CD141,
2.5-50% of the cells in the heterogeneous population of cells express at least one marker selected from the group consisting of: CD303 and CD304,
after activation, 5-50% of the cells in the heterogeneous population of cells express increased intensity of CD141, and
at least 2.5% of the cells in the heterogeneous population of cells express one or more markers selected from the group consisting of: CD31, CD34, and CD184.

For some applications:
the at least 5% of the antigen-presenting cells express at least one marker selected from the group consisting of: CD1c, CD141, CD303, CD304, and CD86.

There is also provided, in accordance with an application of the present invention, a composition of matter, including a population of at least 1 million lineage specific precursor/progenitor cells,
wherein a first subset of the population includes at least 10% of the at least 1 million cells, and expresses one or more markers selected from the group consisting of: CD141, CD303, CD304, and CD86,
wherein a second subset of the population includes at least 10% of the at least 1 million cells, and expresses one or more markers selected from the group consisting of: CD34 and CD184,
wherein a third subset of the population includes at least 10% of the at least 1 million cells, and expresses one or more markers selected from the group consisting of: CD31, CD133, CD144, CD202b, von Willebrand factor (vWF), CD102, CD105, CD106, CD109, CD114 CDw145, CD201, CD299, and CD309,
wherein at least some cells of the population include at least 2.5% of the at least 1 million cells, and express CD309 and CD202b,
wherein at least some cells of the population include at least 5% of the at least 1 million cells, and express CD31 and VEGFR1, and
wherein at least some cells of the population uptake Ac-LDL and express Ulex lectin.

For some applications:
the at least 1 million lineage specific precursor/progenitor cells include at least 5 million lineage specific precursor/progenitor cells,
the third subset of the population expresses CD31, CD202b, CD309, and VEGFR1,
at least 2.5% (e.g., 2.5-70%) of the cells of the third subset of the population of cells uptake Ac-LDL and express Ulex lectin, and
a plurality of cells in the population secrete one or more molecules selected from the group consisting of: G-CSF, SDF-1/CXCR4, IL-8, IL-10, IFN alpha (IFNα), TGF beta (TGFβ), and basic FGF (b-FGF).

For some applications:
at least 2.5% (e.g., 5-55%) of the cells of the first subset of the population of cells express one or more markers selected from the group consisting of: CD303 and CD304,
at least 2.5% (e.g., 2.5-70%) of the cells of the second subset of the population of cells co-express CD34 and CD184, at least some cells of the population include at least 2% of the at least 5 million cells, and express CD31 and CD202b, 2-70% of the cells of the second subset of the population of cells co-express CD31 and CD202b, 2-30% of the cells of the third subset of the population of cells co-express CD309 and CD202b, and 2-30% of the cells of the third subset of the population of cells co-express CD31 and VEGFR1.

There is also provided, in accordance with an application of the present invention, a composition of matter, including a population of at least 1 million lineage specific precursor/progenitor cells, wherein a first subset of the population includes at least 10% of the at least 1 million cells, and expresses one or more markers selected from the group consisting of: CD141, CD303, CD304, and CD86, and wherein a second subset of the population includes at least 10% of the at least 1 million cells, and expresses one or more markers selected from the group consisting of: CD34, CD31, CD202b and CD184.

For some applications:

the at least 1 million lineage specific precursor/progenitor cells include at least 5 million lineage specific precursor/progenitor cells, at least 2.5% (e.g., 5-55%) of the cells of the first subset of the population of cells express one or more markers selected from the group consisting of: CD303 and CD304, at least 2.5% (e.g., 2.5-70%) of the cells of the second subset of the population of cells co-express CD34 and CD184, and at least 2% of the at least 5 million cells express CD31 and CD202b.

For some applications, the composition of matter is frozen.

There is also provided, in accordance with some applications of the present invention, a method including:

obtaining a population of antigen-presenting cells;

enriching a population of stem/progenitor cells within a larger population of cells;

activating the population of antigen-presenting cells; and following the activating, inducing at least one process selected from the group consisting of: differentiation, expansion, activation, secretion of a molecule, and expression of a marker, by exposing the enriched stem/progenitor cell population to the population of antigen-presenting cells.

In some applications, incubating the antigen-presenting cells includes incubating the antigen-presenting cells in a medium including at least one component selected from the group consisting of: CpG OND, IL-10, IL-12, IL-18, IL-27, Alpha-1 Antitrypsin, Flt3 Ligand, IFN alpha (IFNα), IFN beta (IFNβ), Prostaglandin E2 (PGE-2), IL-4, TGF beta (TGFβ) and VEGF.

In some applications, inducing the at least one process includes generating a lineage specific precursor/progenitor population (LSP), and the method further includes administering to a patient one or more compositions selected from the group consisting of: the lineage specific precursor/progenitor population and soluble components of the lineage specific precursor/progenitor population.

In some applications, inducing the at least one process includes inducing differentiation of the enriched population of stem/progenitor cells and inducing expansion of the enriched stem/progenitor cell population.

In some applications, inducing the at least one process includes inducing the at least one process in at least one type of cells selected from the group consisting of: the antigen-presenting cells and the stem/progenitor cells.

In some applications, the population of antigen-presenting cells includes dendritic cells, and obtaining the population of antigen-presenting cells includes obtaining the population of antigen-presenting cells including the dendritic cells, and the antigen-presenting cells direct the at least one process.

In some applications, the method includes activating the enriched population of stem/progenitor cells during the exposing of the enriched population of stem/progenitor cells to the activated population of antigen-presenting cells.

In some applications, inducing the expression of the marker includes increasing a proportion of cells that have at least one characteristic selected from the group consisting of: expression of CD34, expression of CD184, and co-expression of CD34 and CD184.

In some applications, inducing the at least one process includes generating a lineage specific precursor/progenitor (LSP) cell population, and:

at least 2.5% of the LSP cell population express one or more markers selected from the group consisting of: CD31, CD133, CD144, CD202b, von Willebrand factor (vWF), CD102, CD105, CD106, CD109, CD114 CDw145, CD201, CD299, and CD309, at least some of the at least 2.5% of the cells of the population express CD309 and CD202b, at least some of the at least 2.5% of the cells of the population express CD31 and VEGFR1, and at least some of the at least 2.5% of the cells of the population uptake Ac-LDL and expresses Ulex lectin, at least 2.5% of the LSP cell population express one or more markers selected from the group consisting of: CD7, CD31, CD33, CD34, CD90, CD105, CD115, CD117, CDw123, CD124, CD157, CD164, CD172a, CD173, CD175, CD178, CD184, CD191, CD202b, CD292, and Stro-1, and the LSP cell population secretes one or more molecules selected from the group consisting of: G-CSF, SDF-1/CXCR4, IL-8, IL-10, IFN alpha (IFNα), IFN beta (IFNβ), IFN gamma (IFNγ), TGF beta (TGFβ), basic FGF (b-FGF), IL-12, IL-18 and IL-27.

In some applications, activating the population of antigen-presenting cells includes:

separating the antigen-presenting cells from blood, and, subsequently, incubating the antigen-presenting cells for a period of 0.5 hours to 14 days prior to exposing the enriched population of stem/progenitor cells to the population of antigen-presenting cells, following the separating, the antigen-presenting cells are a sub-population of a larger population, and the method further includes increasing a proportion of the antigen-presenting cells in the larger population prior to the incubating.

In some applications, incubating includes incubating the antigen-presenting cells for a period of 0.5 hours to 3 days.

In some applications, increasing the proportion of the antigen-presenting cells includes increasing the proportion to less than 15% of the larger population.

In some applications, activating includes increasing expression of CD141 by the antigen presenting cells.

In some applications, activating includes increasing expression of express one or more markers selected from the group consisting of: CD303 and CD304 by the antigen presenting cells.

In some applications, incubating the antigen-presenting cells includes incubating the antigen-presenting cells for 0.5 hours to 3 days in a medium including at least one component selected from the group consisting of: IL-10, IL-12, IL-18, FGF beta, bFGF, and VEGF.

In some applications, incubating the antigen-presenting cells includes incubating the antigen-presenting cells in a medium including at least one component selected from the group consisting of: IL-10, FGF beta, bFGF, and VEGF, and inducing the at least one process includes increasing a proportion of cells that have at least one characteristic selected from the group consisting of: uptake of AC-LDL combined with expression of Ulex lectin, expression of CD31, expression of CD133, expression of CD144, expression of CD202b (Tie-2), expression of VEGR1, expression of von Willebrand factor (vWF), expression of CD102, expression of CD105, expression of CD106, expression of CD109, expression of CD114, expression of CDw145, expression of CD201, expression of CD299, and expression of CD309 (VEGFR-2; KDR), VEGFR1, co-expression of VEGFR1 and CD31, and co-expression of CD309 and CD202b.

In some applications, the population of stem/progenitor cells includes a population of multipotent adult stem/progenitor cells, and enriching the population of stem/progenitor cells includes enriching the population of multipotent adult stem/progenitor cells.

In some applications, the method includes obtaining the population of multipotent adult stem/progenitor cells from blood.

In some applications, the method includes:
enriching a population of immune effector cells;
following the activating the population of antigen-presenting cells, activating the effector cells by co-culturing the antigen-presenting cells and the effector cells in a co-culture; and
adding to the co-culture the enriched population of stem/progenitor cells, and wherein,
exposing the enriched stem/progenitor cell population to the population of antigen-presenting cells includes exposing the co-culture of the antigen-presenting cells and the effector cells to the enriched stem/progenitor cell population, and
inducing the at least one process includes, responsively to the exposing, creating a lineage-specific precursor/progenitor population.

In some applications, creating the lineage-specific precursor/progenitor population includes creating a lineage-specific precursor/progenitor population having a percentage increase of cytotoxic activity of at least 150%, versus cultured peripheral blood mononuclear cells.

In some applications, the method includes administering to a patient one or more compositions selected from the group consisting of: the lineage-specific population and soluble components of the lineage-specific population.

In some applications, administering the lineage-specific population to the patient includes treating cancer of the patient.

In some applications, creating the lineage-specific precursor/progenitor population includes creating a lineage-specific precursor/progenitor population having at least 10% of cells in the population which express one or more markers selected from the group consisting of: CD86, CD3, CD8, CD4, and CD56.

In some applications, the selected process includes the activation, and the at least 5% of the cells maintain expression of the one or more markers for at least 8 days following the activation.

In some applications, obtaining the antigen-presenting cells includes obtaining a population of at least 50,000 antigen-presenting cells, and at least 5% of the antigen-presenting cells express one or more markers selected from the group consisting of: CD1c, CD1b, CD1e, CD11c, CD40, CD49d, CD53, CD68, CD74, CD80, CD83, CD85, CD86, CDw123, CD172b, CD180, CD141, CD206, CD208, CD209, CD218, CD258, CD301, CD303, and CD304.

In some applications, exposing the enriched stem/progenitor cell population to the population of antigen-presenting cells includes, prior to inducing at least one process, generating a heterogeneous population of cells, and:
the population of antigen-presenting cells is at least 2.5% of the cells in the heterogeneous population,
the population of enriched stem/progenitor cells is at least 1% of the cells in the heterogeneous population of cells, and
at least 1% of the cells in the heterogeneous population of cells express one or more markers selected from the group consisting of: CD7, CD31, CD33, CD34, CD90, CD105, CD115, CD117, CDw123, CD124, CD157, CD164, CD172a, CD173, CD175, CD178, CD184, CD191, CD202b, CD292, and Stro-1.

In some applications, the method includes following the generating the heterogeneous population, freezing the heterogeneous population.

In some applications, generating the heterogeneous population includes generating a heterogeneous population wherein:
the at least 5% of the antigen-presenting cells express one or more markers selected from the group consisting of: CD1c, CD86, CD141, CD303, and CD304, and
the at least 1% of the cells in the heterogeneous population of cells expressing the one or more markers express one or more markers selected from the group consisting of: CD31, CD34, and CD184.

In some applications, generating the heterogeneous population includes generating a heterogeneous population wherein:
the at least 5% of the antigen-presenting cells express at least one marker selected from the group consisting of: CD141, CD303, CD304, and CD86, and
at least 2.5% of the population of enriched stem/progenitor cells express CD34 and CD184 or co-express CD34 and CD184.

In some applications, generating the heterogeneous population includes generating a heterogeneous population:
the at least 5% of the antigen-presenting cells express at least one marker selected from the group consisting of: CD141, CD303, CD304, and CD86, and
the at least 1% of the cells in the heterogeneous population of cells expressing the one or more markers express CD34 and are CD45Dim/−.

In some applications, inducing the at least one process includes generating a population of at least 1 million lineage specific precursor/progenitor cells, wherein:
a first subset of the population includes at least 5% of the at least 1 million cells, and expresses one or more markers selected from the group consisting of: CD1c, CD1b, CD1e, CD11c, CD40, CD49d, CD53, CD68, CD74, CD80, CD83, CD85, CD86, CDw123, CD172b, CD180, CD141, CD206, CD208, CD209, CD218, CD258, CD301, CD303 and CD304,
a second subset of the population includes at least 2.5% of the at least 1 million cells, and expresses one or more markers selected from the group consisting of: CD7, CD31, CD33, CD34, CD90, CD105, CD115, CD117, CDw123, CD124, CD157, CD164, CD172a, CD173, CD175, CD178, CD184, CD191, CD202b, CD292, CD309, VEGFR1, and Stro-1, and
cells in the population secrete one or more molecules selected from the group consisting of: G-CSF, SDF-1/

CXCR4, IL-8, IL-10, IFN alpha (IFNα), IFN beta (IFNβ), IFN gamma (IFNγ), TGF beta (TGFβ), basic FGF (b-FGF), IL-12, IL-18 and IL-27.

In some applications, generating the population includes generating a population in which a portion of cells of the second subset express CD309 and CD202b.

In some applications, generating the population includes generating a population in which a portion of cells of the second subset express CD31 and VEGFR1.

In some applications, generating the population includes generating a population in which a portion of cells of the second subset uptakes Ac-LDL and expresses Ulex lectin.

In some applications, generating the population includes generating a population in which:

the first subset expresses one or more markers selected from the group consisting of: CD141, CD86, CD303, and CD304, and the second subset expresses one or more markers express one or more markers selected from the group: CD34 and CD184.

In some applications, the method includes following the generating the population, freezing the population.

In some applications, inducing the at least one process includes generating a population of at least 1 million lineage specific precursor/progenitor cells, wherein:

a first subset of the population includes at least 10% of the at least 1 million cells, and expresses one or more markers selected from the group consisting of: CD141, CD303, CD304, and CD86, a second subset of the population includes at least 10% of the at least 1 million cells, and expresses one or more markers selected from the group consisting of: CD34 and CD184, a third subset of the population includes at least 10% of the at least 1 million cells, and expresses one or more markers selected from the group consisting of: CD31, CD133, CD144, CD202b, von Willebrand factor (vWF), CD102, CD105, CD106, CD109, CD114 CDw145, CD201, CD299, and CD309, at least some cells of the population includes at least 2.5% of the at least 1 million cells, and expresses CD309 and CD202b, at least some cells of the population includes at least 5% of the at least 1 million cells, and expresses CD31 and VEGFR1, and at least some cells of the population uptakes Ac-LDL and expresses Ulex lectin.

In some applications, the method includes following the generating the population, freezing the population.

There is further provided, in accordance with some applications of the present invention, a composition of matter, including a heterogeneous population of cells, the heterogeneous population of cells including:

(a) a population of at least 50,000 antigen-presenting cells; and (b) a population of enriched stem/progenitor cells, the population of antigen-presenting cells is at least 2.5% of the cells in the heterogeneous population, at least 5% of the antigen-presenting cells express one or more markers selected from the group consisting of: CD1c, CD1b, CD1e, CD11c, CD40, CD49d, CD53, CD68, CD74, CD80, CD83, CD85, CD86, CDw123, CD172b, CD180, CD141, CD206, CD208, CD209, CD218, CD258, CD301, CD303, and CD304, the population of enriched stem/progenitor cells is at least 1% of the cells in the heterogeneous population of cells, and at least 1% of the cells in the heterogeneous population of cells express one or more markers selected from the group consisting of: CD7, CD31, CD33, CD34, CD90, CD105, CD115, CD117, CDw123, CD124, CD157, CD164, CD172a, CD173, CD175, CD178, CD184, CD191, CD202b, CD292, and Stro-1.

In some applications, the at least 5% of the antigen-presenting cells express one or more markers selected from the group consisting of: CD1c, CD86, CD141, CD303, and CD304, and the at least 1% of the cells in the heterogeneous population of cells expressing the one or more markers express one or more markers selected from the group consisting of: CD31, CD34, and CD184.

In some applications, the at least 5% of the antigen-presenting cells express at least one marker selected from the group consisting of: CD141, CD303, CD304, and CD86, and at least 2.5% of the population of enriched stem/progenitor cells express CD34 and CD184.

In some applications, the at least 5% of the antigen-presenting cells express at least one marker selected from the group consisting of: CD141, CD303, CD304, and CD86, and the at least 1% of the cells in the heterogeneous population of cells expressing the one or more markers express CD34 and are CD45Dim/−.

In some applications, the population of enriched stem/progenitor cells includes a population of enriched multipotent adult stem/progenitor cells.

In some applications, the composition of matter is frozen.

There is still further provided, in accordance with some applications of the present invention, a composition of matter, including a population of at least 1 million lineage specific precursor/progenitor cells, a first subset of the population includes at least 5% of the at least 1 million cells, and expresses one or more markers selected from the group consisting of: CD1c, CD1b, CD1e, CD11c, CD40, CD49d, CD53, CD68, CD74, CD80, CD83, CD85, CD86, CDw123, CD172b, CD180, CD141, CD206, CD208, CD209, CD218, CD258, CD301, CD303 and CD304, a second subset of the population includes at least 2.5% of the at least 1 million cells, and expresses one or more markers selected from the group consisting of: CD7, CD31, CD33, CD34, CD90, CD105, CD115, CD117, CDw123, CD124, CD157, CD164, CD172a, CD173, CD175, CD178, CD184, CD191, CD202b, CD292, CD309, VEGFR1, and Stro-1, and cells in the population secrete one or more molecules selected from the group consisting of: G-CSF, SDF-1/CXCR4, IL-8, IL-10, IFN alpha (IFNα), IFN beta (IFNβ), IFN gamma (IFNγ), TGF beta (TGFβ), basic FGF (b-FGF), IL-12, IL-18 and IL-27.

In some applications, a portion of cells of the second subset express CD309 and CD202b.

In some applications, a portion of cells of the second subset express CD31 and VEGFR1.

In some applications, a portion of cells of the second subset uptakes Ac-LDL and expresses Ulex lectin.

In some applications, the first subset expresses one or more markers selected from the group consisting of: CD141, CD86, CD303, and CD304, and the second subset expresses one or more markers express one or more markers selected from the group: CD34 and CD184.

In some applications, the composition of matter is frozen.

There is additionally provided, in accordance with some applications of the present invention, a composition of matter, including a population of at least 1 million lineage specific precursor/progenitor cells, a first subset of the population includes at least 10% of the at least 1 million cells, and expresses one or more markers selected from the group consisting of: CD141, CD303, CD304, and CD86, a second subset of the population includes at least 10% of the at least 1 million cells, and expresses one or more markers selected from the group consisting of: CD34 and CD184, a third subset of the population includes at least 10% of the at least 1 million cells, and expresses one or more markers selected from the group consisting of: CD31, CD133, CD144, CD202b, von Willebrand factor (vWF), CD102, CD105, CD106, CD109, CD114 CDw145, CD201, CD299, and CD309, at least some cells of the population includes at least 2.5% of the at least 1 million cells, and expresses CD309 and CD202b, at least some cells of the population includes at least 5% of the at least 1 million cells, and expresses CD31 and VEGFR1, and at least some cells of the population uptakes Ac-LDL and expresses Ulex lectin.

In some applications, the composition of matter is frozen.

There is yet additionally provided, in accordance with some applications of the present invention, a method including:

obtaining a population of antigen-presenting cells;

enriching a population of stem/progenitor cells from within a larger population of cells; and generating a lineage specific precursor/progenitor (LSP) cell population, by exposing the population of antigen-presenting cells to the population of enriched stem/progenitor cells;

at least 2.5% of the LSP cell population express one or more markers selected from the group consisting of: CD31, CD133, CD144, CD202b, von Willebrand factor (vWF), CD102, CD105, CD106, CD109, CD114 CDw145, CD201, CD299, and CD309, at least some of the at least 2.5% of the cells of the population express CD309 and CD202b, at least some of the at least 2.5% of the cells of the population express CD31 and VEGFR1, and at least some of the at least 2.5% of the cells of the population uptake Ac-LDL and expresses Ulex lectin, at least 2.5% of the LSP cell population express one or more markers selected from the group consisting of: CD7, CD31, CD33, CD34, CD90, CD105, CD115, CD117, CDw123, CD124, CD157, CD164, CD172a, CD173, CD175, CD178, CD184, CD191, CD202b, CD292, and Stro-1, and the LSP cell population secretes one or more molecules selected from the group consisting of: G-CSF, SDF-1/CXCR4, IL-8, IL-10, IFN alpha (IFNα), IFN beta (IFNβ), IFN gamma (IFNγ), TGF beta (TGFβ), basic FGF (b-FGF), IL-12, IL-18 and IL-27.

There is still additionally provided, in accordance with some applications of the present invention, a method including:

obtaining a population of antigen-presenting cells;

enriching a population of stem/progenitor cells from within a larger population of cells; and generating a lineage specific precursor/progenitor (LSP) cell population, by exposing the activated population of antigen-presenting cells to the population of enriched stem/progenitor cells;

at least 10% of the LSP cell population express one or more markers selected from the group consisting of: CD31, CD133, CD144, CD202b, von-Willebrand factor (vWF), CD102, CD105, CD106, CD109, CD114 CDw145, CD201, CD299, VEGFR1, and CD309, and at least 10% of the LSP cell population uptakes Ac-LDL and express Ulex lectin.

In some applications, at least 10% of the LSP cell population uptakes Ac-LDL and expresses Ulex lectin, a first portion of cells of the LSP cell population express CD309 and CD202b, and a second portion of cells of the LSP cell population express CD31 and VEGFR1.

There is further additionally provided, in accordance with some applications of the present invention, a method including:

obtaining a population of antigen-presenting cells;

enriching a population of immune effector cells;

activating the effector cells by co-culturing the antigen-presenting cells and the effector cells in a co-culture;

adding to the co-culture an enriched population of stem/progenitor cells; and creating a lineage-specific precursor/progenitor population by inducing at least one process selected from the group consisting of: differentiation, activation, expansion, secretion of a molecule, and expression of a marker, by exposing the enriched stem/progenitor cell population and the effector cells to the population of antigen-presenting cells.

The present invention will be more fully understood from the following detailed description of embodiments thereof, taken together with the drawings, in which:

DETAILED DESCRIPTION OF EMBODIMENTS

Figure 1:
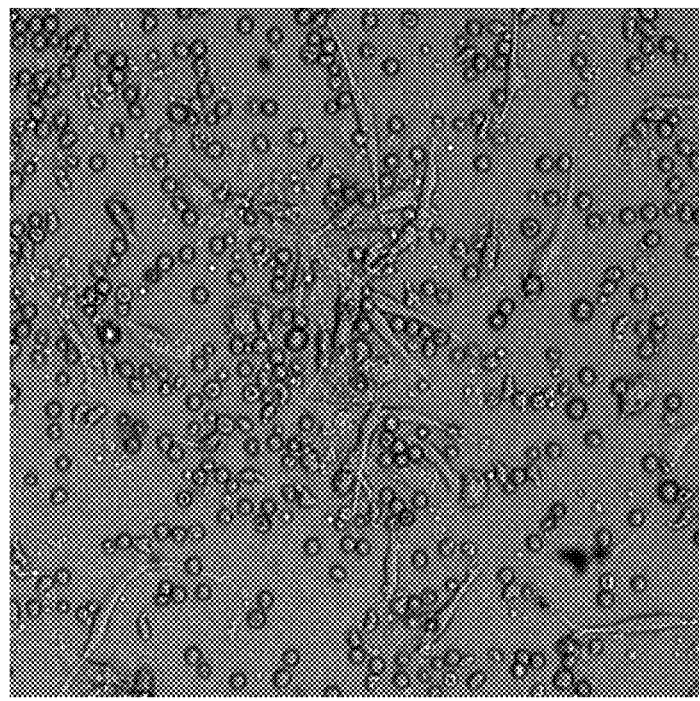
FIG. 1 is a photomicrograph of an LSP, EPC (endothelial progenitor cell)-rich MASPC (multipotent adult stem/progenitor cells) population, generated in accordance with some applications of the present invention.

For some applications, antigen-presenting cells (APC) and/or dendritic cells (DC) are cultured under specific conditions in order to form a directing cell population (DCP) which is used to direct the activation and/or expansion and/or differentiation of cells, in accordance with some applications of the present invention. Initially, the DCP are cultured for a period of between 0.5 hours and 30 days, e.g., between 2 hours and 14 days.

In some applications, incubating the antigen-presenting cells includes incubating the antigen-presenting cells for 0.5 hours to 3 days in a medium including molecules that binds to the cell membrane and sending activation signals to the cells (such as for example cell-cell adhesion, co-stimulatory molecules (tall like receptors) and binding of specific antibodies.

Following the initial culture of the APC and/or DC in order to create the DCP, the DCP is typically then co-cultured with tissue-derived cells (TDC), e.g., multipotent adult stem/progenitor cells (MASPC) or a population of cells containing MASPC, in order to ultimately generate lineage-specific precursors/progenitors (LSP) therefrom. For some applications, DCP are co-cultured with MASPC and subsequently, other TDC cells may subsequently be added to the co-culture of the DCP and MASPC. It is to be noted that for some applications, the DCP is primed prior to co-culturing with the TDC. Priming of the DCP, for some applications, is by means of initially culturing the DCP with MASPC, following which, additional TDC may be added to the co-culture. For some applications, the DCP is co-cultured together with both MASPC and other TDC which may or may not include MASPC. For other applications, following the initial culture of the APC and/or DC in order to create the DCP, the DCP is then co-cultured with MASPC and other TDC.

For some applications, the APC and/or the DCP are initially cultured in conditioned culture medium that is generated from the culturing of stem cells, e.g., MASPC. This may be followed by co-culturing the APC and/or the DCP with stem cells, e.g., MASPC, as described herein. Alternatively, the APC and/or the DCP thus prepared are used for therapeutic, diagnostic, or research purposes following the culturing in conditioned medium, without co-culturing with stem cells.

For some applications, the stem cells, e.g., MASPC, are cultured in conditioned culture medium that is generated from the culturing of APC and/or DCP. This may be followed by co-culturing APC and/or DCP with the stem cells, e.g., MASPC, that have been cultured in the conditioned culture medium. Alternatively, the stem cells are used for therapeutic, diagnostic, or research purposes following the culturing in conditioned medium, without co-culturing with stem cells.

For some applications, the DCP is co-cultured with TDC in order to derive the MASPC.

In either application, during the co-culture of the DCP with the TDC, the DCP induces TDC activation (e.g., proliferation, differentiation, induction of enzymatic activity and induction of biochemical activity, e.g., the secretion of specific molecules and/or the expression of specific markers, e.g., molecular, intracellular and/or membrane markers, etc). It is noted that "inducing" a process, as used herein, includes bringing about an increase in the process or initiating the process. Typically, this activation is used for therapeutic, diagnostic, and research tool. For some applications, the culture medium that is derived from the co-culturing of the DCP with the TDC is administered to a patient (e.g., by injection) for therapeutic purposes.

In some applications, the method includes deriving the DCP and/or the TDC, e.g., MASPC, from at least one source selected from the group consisting of: bone, lymph node, spleen, blood vessel, mucosa, CNS tissue, PNS tissue, cardiac tissue, liver tissue, uterus tissue, adipose tissue, lymphatic tissue, pancreatic tissue, kidney tissue, lung tissue, retinal tissue, embryonic tissue, fetal tissue, umbilical cord blood, umbilical cord tissue, placental tissue, neonatal tissue, adult tissue, bone marrow, mobilized blood, peripheral blood, peripheral blood mononuclear cells, skin cells, and plant tissue.

Typically, the DCP and the TDC, e.g., MASPC, are autologous with respect to the patient. For other applications, the DCP and TDC, e.g., MASPC, are allogeneic with respect to the patient. For yet other applications, the DCP and TDC, e.g., MASPC, are xenogeneic with respect to the patient.

In some applications, the method includes deriving the DCP and TDC, e.g., MASPC, from at least one source selected from the group consisting of: fresh tissue and frozen tissue.

For some applications, the co-culturing of the DCP with the MASPC induces the generation of therapeutic toleragenic cells that can subsequently be implanted in an allogeneic or an autologous acceptor. These toleragenic cells facilitate enhanced engraftment of autologous and/or allogeneic tissues and/or cells. For some applications, the toleragenic cells are generated by culturing the DCP for a period of between 0.5 days and 120 days.

For some applications, the co-culturing of the DCP with the MASPC induces the generation of therapeutic toleragenic cells that can subsequently be implanted in an allogeneic or an autologous acceptor. These toleragenic cells facilitate enhanced engraftment of autologous and/or allogeneic tissues and/or cells. For some applications, the toleragenic cells are generated by culturing the DCP for a period of between 0.5 hours and 48 hours.

For some applications, in order to create these toleragenic cells, the DCP is primed by co-culturing DCP with autologous autoimmune antigens and/or antigens derived from tissues affected by chronic inflammation. During the culture, the DCP is primed when the DCP cells engulf the autoimmune antigens and thereafter present these antigens on the surface of each cell of the DCP. The primed DCP is then co-cultured with TDC, e.g., a population of cells including mature immune cells and MASPC, in order to induce activation thereof. During the co-culture, the DCP presents the autoimmune antigens to mature immune cells of the TDC and/or to the MASPC, in order to generate an LSP, e.g., toleragenic cells used to treat autoimmune disorders and chronic inflammation. The mature immune cells in the LSP are thereby activated by the primed DCP to function immediately as the toleragenic cells. Additionally, the MASPC in the LSP are only primed by the primed DCP to differentiate at a later stage into the very same mature immune cells which function as the toleragenic cells. Thus, the LSP comprises a population of cells which comprise (1) a first subpopulation of cells that are immediately active (i.e., the mature immune toleragenic cells of the LSP in this particular application of the present invention), and (2) a second subpopulation of cells comprising precursors/progenitors which differentiate at a later stage into the cells that are active (i.e., the MASPC).

For some applications, cancer antigens and/or cancer cells are used to prime, or activate, the DCP. The activated DCP is then co-cultured with the TDC and MASPC and presents antigens to the TDC. This co-culture induces the generation of therapeutic numbers of reactive autologous and/or allogeneic anti-tumor cells, as is described hereinbelow and shown in experimental data.

Typically, the DCP induces the expansion, or enrichment, of the cells co-cultured therewith. Additionally, the DCP directs the TDC, e.g., MASPC and other mature cells of the TDC, toward generating an LSP during 2-3 culturing steps:
1. First, the APC and/or DC are cultured under specific conditions in order to create the DCP. These conditions include culturing the APC and/or DC under various environmental conditions, culture in media containing certain factors, culture in conditioned media, co-culture with target tissues, with extracted fractions thereof, and/or with desired cytokine mixtures. Such culturing typically primes and/or activates the DCP;
2. Following the generation, priming, and/or activation of the DCP, one or a combination of the following two steps can be conducted:
   (1) The MASPC is co-cultured together with the activated DCP and activated thereby in response to (a) specific environmental conditions, (b) cell-cell interactions with the primed DCP, and (c) additional activation factors, e.g., growth factors and cytokines. Typically, the activation is expressed by proliferation, differentiation, and/or induction of biochemical activity, etc., of the MASPC; and/or (2) Other TDC (e.g., cells that are not MASPC, such as mature cells of a particular cell type) are added to the culture and are activated thereby as described hereinabove with respect to the activation of the MASPC.

For some applications, steps (1) and (2) may occur sequentially or concurrently. For applications in which steps (1) and (2) are applied, it is to be noted that additional TDC and/or MASPC may be added to the co-culture following step (2) or concurrently therewith. Ultimately, following steps (1) and (2), a population is generated comprising an activated MASPC-rich TDC population. It is to be noted that for some applications, only step (1) is performed without performing step (2).

As a result of the above-listed culturing steps, therapeutic amounts of autologous and/or allogeneic LSP enriched cells and/or soluble molecules thereof can thus be used for tissue regeneration, rejuvenation, and for anti-cancer treatments. In addition, the combinations of cells described herein can be used as diagnostic as well as research tools in order to explore the yet unknown functions of dendritic cells beyond their traditionally-attributed function as regulators of the immune system.

In the context of the present patent application and in the claims, a directing cell population (DCP) is a population of at least 50,000 cells which can be characterized as expressing one or more of the cellular markers: CD1c, CD1b, CD1e, CD11c, CD40, CD49d, CD53, CD68, CD74, CD80, CD83, CD85, CD86, CDw123, CD141, CD172b, CD180, CD206, CD208, CD209, CD218, CD258, CD301, CD303 and CD304.

Typically, following co-culturing of an MASPC-rich TDC population by the activated DCP:

(1) at least 5%, e.g., at least 10%, of the resulting DCP-directed MASPC-rich TDC population expresses:
  (a) one or more of the following co-stimulatory markers: CD1c, CD1b, CD1e, CD11c, CD40, CD49d, CD53, CD68, CD74, CD80, CD83, CD85, CD86, CDw123, CD172b, CD180, CD141, CD206, CD208, CD209, CD218, CD258, CD301, CD303 and CD304,
  and (b) one or more of the following stem/progenitor cell markers CD7, CD31, CD33, CD34, CD90, CD105, CD115, CD117, CDw123, CD124, CD157, CD164, CD172a, CD173, CD175, CD178, CD184, CD191, CD202b, CD292, and Stro-1; and (2) the resulting DCP-directed MASPC-rich TDC population secretes one or more of the following specific molecules: G-CSF, SDF-1/CXCR4, IL-8, and/or IL-10, IFN alpha (IFNα), IFN beta (IFNβ), IFN gamma (IFNγ), TGF beta (TGFβ), basic FGF (b-FGF), IL-12, IL-18, and IL-27.

A DCP is typically, but not necessarily, generated from a hematopoietic source which is typically derived from peripheral blood, e.g., peripheral blood mononuclear cells (PBMC) or cord blood mononuclear cells (CBMC).

Methods described in this patent application disclose the use of APC and DC, taken from the source tissue described hereinabove, to selectively direct stem/progenitor cells into enriched LSP cell populations. The methods described herein include sequential culturing steps in which the APC are first activated to generate DCP that specifically direct expansion and/or differentiation of TDC including but not limited to MASPC at the second and/or third step/s to generate MASPC and/or LSP enriched populations suitable for use as therapeutic and/or diagnostic and/or research tools.

It is to be understood that whereas some applications described herein relate specifically to TDC derived from blood, the scope of the present invention includes techniques for use with stem/progenitor cells derived from a variety of body tissues, mutatis mutandis.

For some applications, the method includes:

(1) collecting a sample of peripheral blood from a donor and/or a patient, isolating and/or enriching mononuclear cells from the sample of peripheral blood, separating populations of: (a) APC cells rich in DC, (b) TDC comprising mature cells of a particular cell type (e.g., effector cells such as monocytes, T cells and/or B cells and/or NK cells), and (c) TDC comprising MASPC from the mononuclear cell fraction, and (2) growing these cells under conditions that will cause the mesenchymal and/or hematopoietic progenitor cells and/or precursors of effector cells present in the mixture of cells (specifically in the MASPC) to differentiate and expand into LSP enriched populations, using techniques described herein such as activating the cell populations with DCP and subsequently culturing the DCP-activated cells under specific culture conditions. Since the number of DCP and LSP in the circulation is typically below 0.1%, the above-listed procedure is conducted ex-vivo in order to sufficiently expand the DCP and LSP cell populations. Following this expansion stage, the cells may be implanted into a patient.

The process of expansion and/or differentiation into specific LSP can be used as a diagnostic tool enabling the detection of abnormalities or pathological conditions of a patient. Pathology of a patient may be indicated if the procedures of expansion and/or differentiation performed on extracted blood (e.g., peripheral blood) or umbilical cord blood of a patient (a) do not produce an LSP, while the same procedures would produce an LSP from cells extracted from a healthy volunteer, or (b) do not produce an LSP that is like an LSP produced from cells extracted from a healthy volunteer.

Furthermore, the process of directed expansion and/or differentiation into specific LSP by the DCP can be used as a research tool to uncover, define, and/or alter mechanisms responsible for specific activation and/or differentiation and/or maturation stages of a cell population taken from a patient.

The following represent methods for use with the extracted blood (e.g., peripheral blood) or umbilical cord blood from the patient. It is to be noted that the following methods may be used independently or in combination:

(1) Isolation of dendritic cells from the blood in accordance with published and/or commercial methodologies for positive selection of cells including but not limited to selection based on binding of specific antibodies (such as CD1a, CD141, CD304, CD303, CDw123, CD172b, CD180, CD141, CD206, CD208, CD209, CD218, CD258, CD301, CD80 and CD86) to a desired cell population;

(2) Enrichment of dendritic cells in accordance with published and/or commercial methodologies for negative selection of cells including but not limited to selection based on binding of specific antibodies (such as CD20, CD3, CD14, CD56, CD97 and CD235) to an undesired cell population;

(3) Enrichment of dendritic cells in accordance with published and/or commercial methodologies for positive selection of cells based on biochemical characteristics of the cells including but not limited to production of specific cytokines (such as IFN, VEGF, IL-10 and IL-12);

(4) Isolation of immature dendritic cells in accordance with published and/or commercial methodologies for positive selection of cells including but not limited to selection based on binding of specific antibodies (such as CD141, CD303, CD301, CD86 and CD304) to a desired cell population;

(5) Enrichment of immature dendritic cells in accordance with published and/or commercial methodologies for negative selection of cells including but not limited to selection based on binding of specific antibodies (such as CD20, CD3, CD14, CD56, CD97 and CD235) to an undesired cell population;

(6) Enrichment of immature dendritic cells in accordance with published and/or commercial methodologies for positive selection of cells including but not limited to selection based on biochemical characteristics of the cells, such as cell adhesion to a plastic surface;

(7) Isolation of plasmacytoid dendritic cells in accordance with published and/or commercial methodologies for positive selection of cells including but not limited to selection based on binding of specific antibodies (such as CD303 and CD304) to a desired cell population;

(8) Enrichment of plasmacytoid dendritic cells in accordance with published and/or commercial methodologies for negative selection of cells including but not limited to selection based on binding of specific antibodies (such as CD20, CD3, CD14, CD56, CD97 and CD235) to an undesired cell population;

(9) Isolation of myeloid dendritic cells based on published and/or commercial methodologies for positive selection of cells including but not limited to selection based on binding of specific antibodies (such as CD1c and CD141) to a desired cell population;

(10) Enrichment of myeloid dendritic cells in accordance with published and/or commercial methodologies for negative selection of cells including but not limited to selection based on binding of specific antibodies (such as CD20, CD3, CD14, CD56, CD97 and CD235) to an undesired cell population;

(11) Isolation of antigen-presenting cells based on published and/or commercial methodologies for positive selection of cells including but not limited to selection based on binding of specific antibodies (such as CD1a-e and CD 13) to a desired cell population; and/or

(12) Enrichment of antigen-presenting cells based on published and/or commercial methodologies for negative selection of cells including but not limited to selection based on binding of specific antibodies (such as CD20, CD3, CD14, CD56, CD97 and CD235) to an undesired cell population.

It is to be noted that mature dendritic cells may also be isolated and applied to a given co-culture.

The above-listed methods may be used independently of or in combination with the following methods for use with extracted blood (e.g., peripheral blood) or umbilical cord blood, including:

(1) Isolation of multipotent adult stem/progenitor cells (MASPC) from TDC (herein, MASPC-rich TDC) in accordance with published and/or commercial methodologies for positive selection of cells including but not limited to selection based on binding of specific antibodies (such as CD184 and CD254) to a desired cell population;

(2) Isolation of MASPC-rich TDC in accordance with published and/or commercial methodologies for positive selection of cells based on biochemical characteristics of the cells including but not limited to the capacity to efflux lipophilic dyes and fluorescent staining of ALDH;

(3) Enrichment of MASPC-rich TDC in accordance with published and/or commercial methodologies for negative selection of cells including but not limited to selection based on binding of specific antibodies (such as CD38, CD20, CD3, CD14, CD56, CD97 and CD235) to an undesired cell population;

(4) Isolation of mesenchymal cells in accordance with published and/or commercial methodologies for positive selection of cells including but not limited to selection based on binding of specific antibodies (such as CD105, Stro-1 and CD271) to a desired cell population;

(5) Enrichment of mesenchymal cells in accordance with published and/or commercial methodologies for negative selection of cells including but not limited to selection based on binding of specific antibodies (such as CD38, CD20, CD3, CD14, CD56, CD97 and CD235) to an undesired cell population;

(6) Isolation of hematopoietic stem/progenitor cells (HSCs) in accordance with published and/or commercial methodologies for positive selection of cells including but not limited to selection based on binding of specific antibodies (such as CD7, CD31, CD34, CD115, CD117, CDw123, CD124, CD133, CD164, CD175, CD184, CD191, and CD202b) to a desired cell population; and/or (7) Enrichment of HSCs in accordance with published and/or commercial methodologies for negative selection of cells including but not limited to selection based on binding of specific antibodies (such as CD38, CD20, CD3, CD14, CD56, CD97 and CD235) to an undesired cell population.

The above-listed methods may be used independently of or in combination with the following methods for use with extracted blood (e.g., peripheral blood) or umbilical cord blood, including:

(1) Isolation of desired tissue derived cells (TDC) such as T Cells and/or B cells and/or NK cells in accordance with published and/or commercial methodologies for positive selection of cells including but not limited to selection based on binding of specific antibodies (such as CD3, CD8, CD20 and CD56) to a desired cell population;

(2) Enrichment of the desired TDC such as T Cells and/or B cells and/or NK cells in accordance with published and/or commercial methodologies for negative selection of cells including but not limited to selection based on binding of specific antibodies to an undesired cell population;

(3) Isolation of effector cells based on published and/or commercial methodologies for positive selection of cells including but not limited to selection based on binding of specific epitopes (such as antibodies directed against a desired cancer epitope) to a desired cell population; and/or (4) Enrichment of effector cells based on published and/or commercial methodologies for negative selection of cells including but not limited to selection based on binding of specific epitopes (such as antibodies specific to cells expressing autoimmune epitopes like for example cells expressing anti-MBP activity) to an undesired cell population.

For some applications, performing the isolation and/or enrichment of APC and/or DC and/or subpopulations thereof includes but is not limited to culturing the DCP cells for a period lasting between 0.5 hours and 14 days, e.g., between 2 hours and 7 days or between 3 days and 14 days.

For some applications, performing the isolation and/or enrichment of APC and/or DC and/or subpopulations thereof includes culturing the DCP cells under tolerance-enhancing conditions, including but not limited to culturing in the presence of IL-10, Alpha-1 Antitrypsin and/or TGFβ, Prostaglandin E2 (PGE-2), and/or IL-4.

For some applications, extracted blood (e.g., peripheral blood) or umbilical cord blood fractions, which include by way of illustration and not limitation DCP and MASPC, can be co-cultured with target tissue or components thereof in order to generate LSP.

For some applications, conditioned medium from cultures of extracted blood (e.g., peripheral blood) or umbilical cord blood fractions, which include by way of illustration and not limitation DCP, can be co-cultured with target tissue or components thereof in order to generate LSP. It is to be understood that the mentioned conditioned medium can be used immediately (i.e., fresh) or after preservation (e.g., by freezing).

For some applications, conditioned medium from cultures of extracted blood (e.g., peripheral blood) or umbilical cord blood fractions, which include by way of illustration and not limitation DCP and MASPC, can be co-cultured with target tissue or components thereof in order to generate LSP. It is to be understood that the mentioned conditioned medium can be used immediately (i.e., fresh) or after preservation (e.g., by freezing).

For some applications, applying the isolation and/or enrichment of the MASPC and/or subpopulations thereof, includes expanding the MASPC percentage and/or number in a resulting population by co-culturing the MASPC with the DCP cells for a period lasting between 2 hours and 7 days.

For some applications, applying the isolation and/or enrichment of the MASPC and subpopulations thereof, includes expanding the MASPC percentage and/or number in a resulting population by co-culturing the MASPC with the DCP cells for a period lasting between 3 days and 120 days.

For some applications, applying the isolation and/or enrichment of MASPC and/or subpopulations thereof, includes expanding the MASPC percentage and/or number in a resulting population by co-culturing the MASPC with the DCP cells for a period lasting between 2 hours and 120 days.

For some applications, TDC, e.g., MASPC, are co-cultured with DCP cells for a period lasting between 2 hours and 7 days in order to generate, and increase the proportion and number of a given resultant LSP.

For some applications, TDC, e.g., MASPC, are co-cultured with DCP cells for a period lasting between 3 hours and 120 days in order to generate, and increase the proportion and number of a given resultant LSP.

For some applications, the DCP and/or the TDC, e.g., MASPC, are cultured under conditions, including but not limited to culturing in the presence of less than 5% serum, e.g., 0% serum, for 2-60 days, followed by culturing of cells in the presence of greater than or equal to 5% serum between 1 and 60 days.

In some applications, the DCP and/or the TDC e.g., MASPC, are cultured under conditions, including but not limited to culturing the cells in the presence of greater than or equal to 5% serum between 1 and 60 days, followed by culturing the cells in the presence of less than 5% serum between 2-60 days.

For some applications, the DCP and/or the TDC, e.g., MASPC, are cultured under conditions, including but not limited to culturing in the presence of hypoxic conditions for 2-96 hours before and/or after culturing of cells in the presence of non-hypoxic conditions between 1 and 60 days.

For some applications, the DCP and/or the TDC, e.g., MASPC, are cultured under conditions, including but not limited to culturing in the presence of hypothermic conditions (e.g., less than or equal to 26 degrees C.) for 2-96 hours, before and/or after culturing of cells in the presence of non-hypothermic conditions between 1 and 60 days.

For some applications, the DCP, and/or the TDC, e.g., MASPC, are cultured under conditions, including but not limited to culturing in the presence of hyperthermic conditions (e.g., greater than or equal to 41 degrees C.) 2-96 hours before and/or after culturing of cells in the presence of non-hyperthermic conditions between 1 and 60 days.

For some applications, the DCP and/or the TDC, e.g., MASPC, are cultured under conditions, including but not limited to culturing in the presence of less than 3% $CO_2$ between 2-48 hours before and/or after culturing of cells in the presence of greater than or equal to 5% $CO_2$ between 1 and 14 days.

For some applications, the DCP and/or the TDC e.g., MASPC, are cultured under maturation-inducing conditions, including but not limited to culturing in the presence of growth-enhancing, activation, differentiation, and/or directing molecules. Typically, such molecules are presented to the cells as soluble and/or aggregated molecules in the culture medium. Alternatively or additionally, these molecules are presented to the cells as immobilized molecules including but not limited to molecules that are immobilized on carrier particles (e.g., biodegradable matrices and tissue extracts) and/or molecules bound to the surface of the culture dish.

For some applications, the DCP and/or the TDC, e.g., MASPC, are cultured under maturation-inducing conditions, including but not limited to culturing the cells in the presence of one or more of the following activation molecules: CpG OND, IL-10, IL-12, IL-18, IL-27, Alpha-1 Antitrypsin, Flt3 Ligand, IFNα, IFNβ, IFNγ Prostaglandin E2 (PGE-2), IL-4, b-FGF, and/or TGFβ.

For some applications, the DCP and/or the TDC, e.g., MASPC are cultured on a surface including by way of illustration and not limitation one or more of the following growth-enhancing factors: collagen, fibronectin, albumin, plasma and/or serum.

In some applications the DCP and/or the TDC, e.g., MASPC are cultured under specific conditions which mimic conditions present in tissue in-vivo. For example, the cells are cultured in a medium comprising one or more of the following tissue-derived factors by way of illustration and not limitation: antibodies, cytokines, growth factors, tissue-derived extra cellular matrix, and/or other molecules, such as: anti-CD34, anti-Tie-2, anti-CD133, anti-CD117, LIF, EPO, IGF, b-FGF, M-CSF, GM-CSF, TGF alpha, TGF beta, VEGF, BHA, BDNF, NGF, NT3, NT4/5, GDNF, S-100, CNTF, EGF, NGF3, CFN, ADMIF, Alpha-1 Antitrypsin, estrogen, cortisone, dexamethasone, or any other molecule from the steroid family, prolactin, an adrenocorticoid, glutamate, serotonin, acetylcholine, NO, retinoic acid (RA), heparin, insulin, forskolin, a statin, or an anti-diabetic drug (e.g., a thiazolidinedione such as rosiglitazone), NO, MCDB-201, sodium selenite, linoleic acid, ascorbic acid, transferrin, 5-azacytidine, PDGF, VEGF, cardiotrophin, and/or thrombin.

It is to be appreciated that the particular stimulation factors described herein are by way of illustration and not limitation, and the scope of the present invention includes the use of other stimulation factors. As appropriate, these factors may be utilized in a concentration of between about 10 pg/ml and about 100 ug (microgram)/ml (or molar equivalents).

For some applications, the DCP and/or the TDC, e.g., MASPC are cultured under one or more of the following maturation-inducing conditions, including but not limited to culturing in the presence of one or more antibodies, e.g., anti-CD4, anti-CD19, anti-CD38, anti-CD220, anti-CD221, and/or anti-CD222.

For some applications, the method for culturing the DCP and/or the TDC, e.g., MASPC includes culturing the cells with one or more of the following specific activation-inducing components which are extracted from a target tissue including but not limited to: cellular fractions, specific extracted membrane elements, specific extracted receptors, and/or specific extracted antigenic molecules.

For some applications, the DCP and/or the TDC e.g., MASPC are co-cultured together with a target tissue under specific activation conditions. For some applications, the target tissue is in direct contact with the DCP and/or the TDC, e.g., MASPC. Alternatively, the target tissue is separated from the DCP and/or the TDC, e.g., MASPC by a semipermeable membrane.

A target tissue, in the context of the present patent application and in the claims, is typically, but not necessarily, a tissue representing a desired final state of the progenitor cells in the culture. Alternatively or additionally, a target tissue is a tissue obtained from damaged tissue (e.g., from burned skin tissue, cancerous infected tissue, tissue infected by autoimmune disease, tissue infected by chronic inflammation, etc.). In such some applications, the cells co-cultured with the damaged tissue are directed via the DCP to differentiate into healthy cells of the tissue so as to heal the damaged tissue following administration.

As appropriate, the target tissue may be autologous, syngeneic, allogeneic, or xenogeneic with respect to the source tissue from which the cultured DCP, TDC, and/or MASPC were produced. Alternatively or additionally, the DCP and/or the TDC, e.g., MASPC are cultured in a conditioned medium made using the target tissue which is autologous, syngeneic, allogeneic, or xenogeneic with respect to the source tissue from which the cultured DCP and/or the TDC, e.g., MASPC were produced.

For some applications, the target tissue is co-cultured with the DCP and/or the TDC, e.g., MASPC in the conditioned medium. It is noted that the source of the target tissue may also be tissue from embryonic tissue, fetal tissue, umbilical cord blood, umbilical cord tissue, placental tissue, neonatal tissue, adult tissues such as bone marrow, mobilized blood, peripheral blood, peripheral blood mononuclear cells, lymph node, spleen, liver, uterus, fat tissue, skin cells, pancreas, kidney, lung, retina, CNS, peripheral nervous system, mucosa, cardiac tissue and plant tissue, a cadaver, and/or may be lyophilized, fresh, or preserved.

For some applications, following stimulation by the DCP, the resulting DCP-directed MASPC (i.e., the LSP) express co-stimulatory molecules such as CD11c, CD40, CD80 and CD86 and secrete specific molecules such as G-CSF, SDF-1/CXCR4, IL-8, IL-10.

For some applications, following co-culturing and activation of TDC, e.g., MASPC, with stimulated DCP, the resultant LSP is tested to verify that it has differentiated and/or expanded into a desired form. Characterization of differentiated cells is performed according to the cells' phenotypical, genotypical and physiological features. In accordance with some applications of the present invention, cells are characterized by assessing the functional/physiological activity thereof, in addition to or instead of evaluating the presence or absence of certain cellular markers. The inventor hypothesizes that evaluating functional/physiological activity of LSP cells increases the likelihood that the product obtained and designated for in-vivo use will perform as expected.

For some applications, the LSP and/or soluble molecules thereof are used as a therapeutic cell product (e.g., for cancer therapy, for enhancement of allogeneic tissue engraftment, for tissue and or tissue-function regeneration, for tissue engineering, for tissue replacement, for treatment of autoimmune, allergy, chronic inflammation and/or other immunological disorders), as a research tool (e.g., for research of signal transduction, or for screening of growth factors), and/or as a diagnostic tool.

When the LSP are used as a therapeutic cell product, they are typically administered to a patient. Once administered, the progenitor cells mature into a given desired cell type (e.g., endothelial cells, retinal cells, etc.). For some applications, a therapeutic cell product is administered to an allogeneic patient other than from the human from whom the TDC were obtained.

For some applications, the LSP are assessed for one or more of the following physiological characteristics including but not limited to: enzymatic reactions, secretion of factors (e.g., cytokines), migration capability, induction of migration of stem cells, and/or generation of cell colonies.

For some applications, the LSP are transfected with a gene and are then administered to a patient.

In some applications, the method includes identifying the LSP as being suitable for therapeutic use in response to an assessment that the LSP includes at least 5 million specific LSP cells e.g., 5 million cells.

In some applications, the method includes identifying the LSP as being suitable for therapeutic use in response to an assessment that at least 2.0% of cells of the LSP demonstrate a feature selected from the group consisting of: a desired morphology, a desired cellular marker, a desired cellular component, a desired enzyme, a desired receptor, a desired genotypic feature, and a desired physiological feature.

It is to be noted that the indications described hereinabove are only examples of the therapeutic uses of a LSP, comprising transplantation of LSP (such as EPC-rich LSP or a LSP-aCCP) to a vicinity of tissue or a space of a subject selected from the group consisting of: tissue of a peripheral nerve of the subject, tissue of a central nervous system nerve of the subject, an optic nerve of the subject, choroid tissue of the subject, retinal tissue of the subject, sub-retinal space of the subject, corneal tissue of a subject, kidney tissue of the subject, pancreatic tissue of the subject, lung and alveolar tissue of the subject, tissue of a damaged bone of the subject, tissue of a fractured bone of the subject, inflamed tissue of the subject, infected tissue of the subject, contused tissue of the subject, damaged, ulcerated or wounded tissue of a skin of, brain tissue of the subject, tissue of a limb of the subject, tissue of a skin graft, and/or tissue of a reattached severed limb of the subject.

In some applications, the cultured cells may be used as a diagnostic tool. For some applications, a product of any given stage in the processes described herein is used as a diagnostic tool.

Pathology of a patient may be indicated if an in-vitro procedure performed on extracted blood (e.g., peripheral blood) or umbilical cord blood of the patient does not produce a DCP, while the same procedure would produce a DCP from cells extracted from a healthy volunteer.

Alternatively or additionally, a pathology of a patient may be indicated if an in-vitro stimulation procedure performed on an autologous DCP and/or co-culture of DCP and TDC does not produce a desired LSP, when the same procedure would produce the desired number of a desired LSP from DCP and/or co-culture of DCP and TDC of a healthy volunteer.

Alternatively or additionally, pathology of a patient may be indicated if one or more in-vitro protocols used to assess a DCP do not yield the same results as a DCP originated from a healthy volunteer.

Further alternatively or additionally, pathology of a patient may be indicated if one or more in vitro protocols used to assess a LSP do not yield the same results as a LSP originated from a healthy volunteer.

Yet further alternatively or additionally, a pathology of a patient may be indicated if one or more protocols used to assess a LSP following implantation in a patient do not perform as expected (i.e., does not perform as an LSP would if implanted in a healthy animal or human volunteer).

For some applications, the cultured cells are used as research tools. In such applications, the mammalian cell donor may be human or non-human, as appropriate.

In some applications, stimulating the DCP and the TDC, e.g., MASPC, includes directing the DCP, TDC, and/or MASPC to differentiate into a pre-designated, desired class of LSP.

For some applications, an effort is made to minimize the time elapsed from collection of cells from the cell donor until the LSP are used (e.g., for administration into a patient). Alternatively, cells are preserved at one or more points in the process. For example, the DCP and/or the TDC, e.g., MASPC may be frozen prior to the stimulation thereof that generates LSP. In another example, the DCP and/or TDC and/or MASPC are stimulated in order to generate desired LSP, and the LSP are then frozen. In either of these cases, the frozen cells may be stored and/or transported, for subsequent thawing and use.

By way of illustration and not limitation, it is noted that certain applications are suitable for large-scale commercialization, including freezing and transport, such as (a) generation of stores of DCP, TDC and/or MASPC, and/or soluble molecules thereof (b) generation of stores of LSP, for possible later use. Other applications that use autologous and/or allogeneic cell administration (such as acute post-stroke damage, spinal cord injury, tissue regeneration, and tissue rejuvenation) may benefit from the availability of stored cells. "Transport," in this context, means transport to a remote site, e.g., a site greater than 10 km or 100 km away from a site where the DCP and/or TDC and/or MASPC and/or the LSP were first created.

One example of such an LSP that is described herein and shown in the experimental data, is a lineage-specific population which contains a population of cells which demonstrate increased cytotoxic activity toward cancer cells. Tissue-derived cells (TDC), including MASPC and effector cells such as T cells and/or natural killer cell, are activated by the DCP to produce a lineage-specific, anti-cancer cell progenitor population (LSP-aCCP). The LSP-aCCP contains a population of mature activated effector cells as well as a population of precursor cells that are directed to eventually differentiate into mature activated effector cells. In such a manner, the LSP-aCCP contains cells that are available for immediate anti-cancer use as well as a sub-population of latent cells which can replenish the mature activated effector cells by differentiating into the mature activated effector cells at a later stage. The LSP-aCCP may be produced, treated, and/or administered to a patient, using any one of the techniques described herein.

Another example of such an LSP that is described herein and shown in the experimental data, is a lineage-specific population which contains a population of cells which include endothelial progenitors/precursors (EPC). Tissue-derived cells (TDC), including MASPC are activated by the DCP to produce an EPC-rich LSP. The EPC-rich LSP contains a population of EPCs as well as a population of cells that are directed to eventually differentiate into EPCs (i.e., additional MASPC that have not yet differentiated). In such a manner, the EPC-rich LSP contains cells that are available immediately as EPCs as well as a sub-population of latent cells which can replenish the EPCs by differentiating into EPCs cells at a later stage (i.e., MASPC). Therefore, the LSP that is created comprises an EPC-rich MASPC population.

Methods Used for Some Applications of the Present Invention

A series of protocols are described hereinbelow, which may be used separately or in combination, as appropriate, in accordance with applications of the present invention. It is to be appreciated that numerical values are provided by way of illustration and not limitation. Typically, but not necessarily, each value shown is an example selected from a range of values that is within 20% of the value shown. Similarly, although certain steps are described with a high level of specificity, a person of ordinary skill in the art will appreciate that other steps may be performed, mutatis mutandis.

1. In accordance with some applications of the present invention, generation of a single-cell suspension of tissue derived cells (TDC) is carried out using one or more of the following protocols:

EXAMPLE 1.1

Extraction of Peripheral Blood Mononuclear Cells (PBMC)

Receive blood bag and sterilize it with 70% alcohol.
Load blood cells onto a FICOLL™ gradient.
Spin the tubes for 20 minutes at 1050 g at room temperature (RT), with no brake.
Collect most of the plasma from the upper layer.
Collect the white blood cell fraction from every tube.
Transfer the collected cells to a new 50 ml tube, adjust volume to 30 ml per tube using PBS.
Spin tubes for 15 minutes at 580 g, RT, and discard supernatant.
Count suspended cells, possibly in hemocytometer, assess viable cells using trypan blue.
Re-suspend in culture medium comprising, for example, X-VIVO 15™ and BIOTARGET-1™.

EXAMPLE 1.2

Extraction of Cells from Umbilical Cord

Take 10 cm umbilical cord.
Wash thoroughly with sterile PBS.
Identify the big vein of the cord, and close one end of the vein using clamps.
Wash twice with 30 ml sterile PBS.
Fill vein with 0.15% collagenase (about 5 ml of 0.15% collagenase solution).
Close the second end of the vein using clamps.
Incubate at 37 degrees C. for 15 min
Wash outer side of the cord with 70% ethanol.
Untie the clamps from one end and collect cell suspension.
Centrifuge for 10 min at 580 g, 21 degrees C.
Re-suspend in culture medium comprising, for example, X-VIVO 15™ and BIOTARGET-1™, 10% autologous serum, 5 IU/ml heparin, and one or more growth factors.

EXAMPLE 1.3

Extraction of Umbilical Cord-blood Mononuclear Cells (CBMC)

Receive blood bag and sterilize it with 70% alcohol.
Load blood cells onto a FICOLL™ gradient.
Spin the tubes for 20 minutes at 1050 g at room temperature (RT), with no brake.
Collect most of the plasma from the upper layer.
Collect the white blood cell fraction from every tube.
Transfer the collected cells to a new 50 ml tube, adjust volume to 30 ml per tube using PBS.

Spin tubes for 15 minutes at 580 g, RT, and discard supernatant.

Count suspended cells, possibly in hemocytometer, assess viable cells using trypan blue.

Re-suspend in culture medium comprising, for example, X-VIVO 15™ and BIOTARGET-1™.

EXAMPLE 1.4

Extraction of Cells from Bone Marrow

Obtain bone marrow aspiration from surgical room.
Suspend 1:4 in sterile PBS.
Load cells onto a FICOLL™ gradient.
Spin the tubes for 20 minutes at 1050 g at room temperature (RT), with no brake.
Collect most of the upper layer.
Collect cell from the interphase fraction.
Transfer the collected cells to a new 50 ml tube, adjust volume to 30 ml per tube using PBS.
Spin tubes for 15 minutes at 580 g, RT, and discard supernatant.
Count suspended cells, possibly in hemocytometer, assess viable cells using trypan blue.
Re-suspend in culture medium comprising, for example, X-VIVO 15™ and BIOTARGET-1™, 10% autologous serum, 5 IU/ml heparin, and one or more growth factors.
Pass suspension through a 200 um (micrometer) mesh.
2. In accordance with some applications of the present invention, isolation of desired cells is carried out using one or more of the following protocols:

EXAMPLE 2.1

Isolation of Hematopoietic Stem and Progenitor Cells

Isolation of hematopoietic stem and progenitor cells using a positive selection commercial kit (such as "CD34 MultiSort Kit" by Miltenyi Biotec. 130-056-701 or alternative).

EXAMPLE 2.2

Enrichment of Hematopoietic Stem and Progenitor Cells

Isolation of hematopoietic stem and progenitor cells using a negative selection commercial kit (such as "Lineage Cell Depletion Kit human" by Miltenyi Biotec. 130-092-211 or alternative).

EXAMPLE 2.3

Enrichment of Non-Hematopoietic Stem and Progenitor Cells

Isolation of non-hematopoietic stem and progenitor cells using positive selection commercial antibodies such as CD105, Stro-1 and CD271 ("CD105 Microbeads human" by Miltenyi Biotec. 130-051-201 or alternative).

EXAMPLE 2.4

Isolation of Stem and Progenitor Cells

Isolation of stem and progenitor cells using a positive selection based on magnetic beads with a panel of antibodies including CD34, CD184, and CD254. Isolation is performed using published procedures for negative selection of cell populations.

Prepare a solution containing phosphate-buffered saline (PBS), pH 7.2, 0.5% bovine serum albumin (BSA), and 2 mM EDTA. Keep buffer cold (2-8 degrees C.).
Count suspended cells, possibly in hemocytometer; assess viable cells using trypan blue.
Spin cell suspension 300 g 10 minutes, RT. Pipette off supernatant completely.
Re-suspend cell pellet in 300 ul (microliter) buffer.
Add 100 ul (microliter) FcR blocker.
Add magnetic beads tagged antibodies against CD34, CD184, and CD254.
Incubate 15 minutes at 4-8 degrees C.
Wash cells by adding 10 ml buffer and spin at 300 g 10 minutes, RT Pipette off supernatant completely.
Re-suspend cell pellet in 500 ul (microliter) buffer.
Load cells on separation tube/column
Pipette off the non bound cell fraction.
Detach separation tube/column from the magnetic field
Wash cells by adding 10 ml buffer and spin at 300 g 10 minutes, RT Pipette off supernatant completely.
Count suspended cells, possibly in hemocytometer, assess viable cells using trypan blue.
Re-suspend cell pellet in medium.
Cells are ready for use.

EXAMPLE 2.5

Isolation of Effector Cells

Isolation of CD8-positive, TCR-negative cells using a procedure of negative and positive selection based on magnetic beads. Depletion of TCR-positive cells is followed by isolation of CD8 cells. Isolation is done using published procedures for negative and positive selection of cell populations, in accordance with the following protocol (shown by way of illustration and not limitation).

Protocol:
a. Prepare a solution containing phosphate-buffered saline (PBS), pH 7.2, 0.5% bovine serum albumin (BSA), and 2 mM EDTA. Keep buffer cold (2-8 degrees C.).
b. Count suspended cells, possibly in hemocytometer, assess viable cells using trypan blue.
c. Spin cell suspension 300 g 10 minutes, RT. Pipette off supernatant completely.
d. Re-suspend cell pellet in 300 ul (microliter) buffer.
e. Add 100 ul (microliter) FcR blocker.
f. Add magnetic beads tagged antibodies against TCR alpha, TCR beta, TCR gamma, and TCR delta.
g. Incubate 15 minutes at 4-8 degrees C.
h. Wash cells by adding 10 ml buffer and spin at 300 g 10 minutes, RT Pipette off supernatant completely.
i. Re-suspend cell pellet in 500 ul (microliter) buffer.
j. Load cells on separation tube/column
k. Collect the non bound cell fraction.
l. Wash cells by adding 10 ml buffer and spin at 300 g 10 minutes, RT Pipette off supernatant completely.
m. Count suspended cells, possibly in hemocytometer, assess viable cells using trypan blue.
n. Spin cell suspension 300 g 10 minutes, RT. Pipette off supernatant completely.
o. Re-suspend cell pellet in 300 ul (microliter) buffer.
p. Add 100 ul (microliter) FcR blocker.
q. Add magnetic beads tagged antibodies against CD8.
r. Incubate 15 minutes at 4-8 degrees C.

s. Wash cells by adding 10 ml buffer and spin at 300 g 10 minutes, RT Pipette off supernatant completely.
t. Re-suspend cell pellet in 500 ul (microliter) buffer.
u. Load cells on separation tube/column
v. Pipette off the non bound cell fraction.
w. Detach separation tube/column from the magnetic field.
x. Wash cells by adding 10 ml buffer and spin at 300 g 10 minutes, RT Pipette off supernatant completely.
y. Count suspended cells, possibly in hemocytometer, assess viable cells using trypan blue.
z. Re-suspend cell pellet in medium.
aa. Cells are ready for use.

EXAMPLE 2.6

Isolation of Stem and Progenitor Cells

Isolation of stem and progenitor cells using a negative selection based on magnetic beads with a panel of antibodies including CD8, CD56, and CD20. Isolation is performed using published procedures for negative selection of cell populations, in accordance with the following protocol (shown by way of illustration and not limitation).
Protocol:
a. Prepare a solution containing phosphate-buffered saline (PBS), pH 7.2, 0.5% bovine serum albumin (BSA), and 2 mM EDTA. Keep buffer cold (2-8 degrees C.).
b. Count suspended cells, possibly in hemocytometer, assess viable cells using trypan blue.
c. Spin cell suspension 300 g 10 minutes, RT. Pipette off supernatant completely.
d. Re-suspend cell pellet in 300 ul (microliter) buffer.
e. Add 100 ul (microliter) FcR blocker.
f. Add magnetic beads tagged with specific antibodies against the desired marker.
g. Incubate 15 minutes at 4-8 degrees C.
h. Wash cells by adding 10 ml buffer and spin at 300 g 10 minutes, RT Pipette off supernatant completely.
i. Re-suspend cell pellet in 500 ul (microliter) buffer.
j. Load cells on separation tube/column
k. Collect the non bound cell fraction.
l. Wash cells by adding 10 ml buffer and spin at 300 g 10 minutes, RT Pipette off supernatant completely.
m. Count suspended cells, possibly in hemocytometer, assess viable cells using trypan blue.
n. Re-suspend cell pellet in medium.
o. Cells are ready for use.
For this particular example, the desired markers against which the antibodies are applied in step f, are CD20, CD8, and CD56.

EXAMPLE 2.7

Isolation of Stem and Progenitor Cells

Depletion of red blood cells (RBC) can be used individually or in combination with other methods described hereinbelow.

EXAMPLE 2.7.1

RBC Depletion Using RBC Lysis H$_2$O (Water)

Protocol:
a. Spin cells 7 min 300 g; RT. Pipette off supernatant completely.
b. Lyse the cells with 0.5-2.0 ml sterile H$_2$O (water) per 100*10^6 cells for 2-5 min
c. Add 40 ml cold PBS.
d. Spin cells 7 min 300 g; RT. Pipette off supernatant completely.
e. Resuspend the pellet in the appropriate buffer for use in the next step.

EXAMPLE 2.7.2

Depletion of RBC and Immature RBC Based on Specific Cellular Molecules

A negative selection based on magnetic beads with a panel of antibodies including at least one of the following CD71 (transferring receptor) and CD235a. Negative selection is performed using published procedures for negative selection of cell populations, in accordance with the following protocol (shown by way of illustration and not limitation):
Protocol:
a. Prepare a solution containing phosphate-buffered saline (PBS), pH 7.2, 0.5% bovine serum albumin (BSA), and 2 mM EDTA. Keep buffer cold (2-8 degrees C.).
b. Count suspended cells, possibly in hemocytometer, assess viable cells using trypan blue.
c. Spin cell suspension 300 g 10 minutes, RT. Pipette off supernatant completely.
d. Re-suspend cell pellet in 300 ul (microliter) buffer.
e. Add 100 ul (microliter) FcR blocker.
f. Add magnetic beads tagged with specific antibodies against the desired marker.
g. Incubate 15 minutes at 4-8 degrees C.
h. Wash cells by adding 10 ml buffer and spin at 300 g 10 minutes, RT Pipette off supernatant completely.
i. Re-suspend cell pellet in 500 ul (microliter) buffer.
j. Load cells on separation tube/column
k. Collect the non bound cell fraction.
l. Wash cells by adding 10 ml buffer and spin at 300 g 10 minutes, RT Pipette off supernatant completely.
m. Count suspended cells, possibly in hemocytometer, assess viable cells using trypan blue.
n. Re-suspend cell pellet in medium.
o. Cells are ready for use.
3. In accordance with some applications of the present invention, isolation and/or enrichment of antigen-presenting cells (APC) and/or dendritic cells (DC) is carried out using one or more of the following protocols:

EXAMPLE 3.1

Isolation of Immature DC

Isolation of immature DC based on BCDA-3 (CD141) and BDCA-4 (CD304) using a commercial kit (such as "Blood Dendritic Cell Isolation Kit human"; Miltenyi Biotec Cat. no. 130-091-379 or alternative).

EXAMPLE 3.2

Enrichment of DC

Enrichment of DC based on depletion of non-DC cells by using magnetic beads with a panel of antibodies including CD20, CD3, CD14, CD56, CD97 and CD235. Enrichment is performed using published procedures for negative selection of cell populations, in accordance with the protocol listed in Example 2.6.

For this particular example, the desired markers against which the antibodies are applied in step f, are CD20, CD3, CD14, CD56, CD97 and CD235.

EXAMPLE 3.3

Enrichment of APC and DC

Enrichment of DC Based on Adhesion to Plastic Surface
Spin down cell suspension 300 g 10 min, RT. Pipette off supernatant completely.
Count suspended cells, possibly in hemocytometer, assess viable cells using trypan blue.
Re-suspend cell pellet to concentration of 2-20 million/ml in PBS (or serum free medium).
Float plastic surface of a Petri dish with 5 ml suspended cells.
Incubate for 2 hours at 37 degrees C.
Aspirate out the non-adherent cells and pipette off supernatant completely.
Add 5 ml cold PBS and harvest adherent cells by gentle scraping.
Count suspended cells, possibly in hemocytometer, assess viable cells using trypan blue.
Spin down cell suspension 300 g 10 minutes, RT. Pipette off supernatant completely.
Re-suspend cell pellet in medium.
Cells are ready for use.

EXAMPLE 3.4

Isolation of Immature DC

Enrichment of DC based on positive selection of DC cells by using magnetic beads with at least one of the following antibodies: CD1a, CD1c, CD11c, CD141, CD304, CD303, CDw123, CD172b, CD180, CD141, CD206, CD208, CD209, CD218, CD258, CD301, CD80, and CD86. Isolation is performed using published procedures for positive selection of cell populations, in accordance with the following protocol (shown by way of illustration and not limitation).
Protocol:
a. Prepare a solution containing phosphate-buffered saline (PBS), pH 7.2, 0.5% bovine serum albumin (BSA), and 2 mM EDTA. Keep buffer cold (2-8 degrees C.).
b. Count suspended cells, possibly in hemocytometer, assess viable cells using trypan blue.
c. Spin cell suspension 300 g 10 minutes, RT. Pipette off supernatant completely.
d. Re-suspend cell pellet in 300 ul (microliter) buffer.
e. Add 100 ul (microliter) FcR blocker.
f. Add magnetic beads tagged with specific antibodies against the desired marker.
g. Incubate 15 minutes at 4-8 degrees C.
h. Wash cells by adding 10 ml buffer and spin at 300 g 10 minutes, RT Pipette off supernatant completely.
i. Re-suspend cell pellet in 500 ul (microliter) buffer.
j. Load cells on separation tube/column
k. Collect the non-bound (negative selection) cell fraction.
l. Collect positive selection cells: Remove column from the separator and place it the DC tube.
m. Quickly add 5 ml medium (such as for example, X-VIVO15+IL-10), flash all cells from the column using the siring plunger.
n. Wash cells by adding 10 ml buffer and spin at 300 g 10 minutes, RT Pipette off supernatant completely.
o. Count suspended cells, possibly in hemocytometer, assess viable cells using trypan blue.
p. Re-suspend cell pellet in medium.
q. Cells are ready for use.
For this particular example, the desired markers against which the antibodies are applied in step f, are CD20, CD3, CD14, CD56, CD97 and CD235.

EXAMPLE 3.5

Isolation of Immature Plasmacytoid DC

Isolation of DC using a commercial kit (such as "Plasmacytoid dendritic isolation kit human" by Miltenyi Biotec. 130-092-207 or alternative).

EXAMPLE 3.6

Isolation of Immature Myeloid DC

Isolation of immature myeloid DC using a commercial kit (such as "CD1c (BDCA-1)+Dendritic Cell Isolation Kit human" by Miltenyi Biotec. 130-090-506 or alternative).
4. In accordance with some applications of the present invention, coating of the tissue culture surface is carried out using one or more of the following protocols:

EXAMPLE 4.1

Coating Petri-dish with 25 ug/ml Fibronectin

Prepare up to seven days before, or on day of cell preparation.
Prepare 50 ml of 25 ug/ml fibronectin solution in PBS.
Fill every dish with 0.5-2.5 ml fibronectin 25 ug/ml.
Incubate at 37 degrees C. for at least 30 min.
Collect fibronectin solution.
Wash Petri dish twice in PBS.
Dry the Petri dish.
Keep dry flasks at room temperature.
Dried flasks can be saved for one week at room temperature (RT).

EXAMPLE 4.2

Coating T75 Flasks with 20 ng per ml IL-3

Prepare 20 ml of 20 ng per ml IL-3 solution in PBS.
Fill every flask with 2-5 ml IL-3 solution.
Incubate at 37 degrees C. for 0.5 hours.
Collect the solution.
Wash flask twice in 10 ml PBS.
Keep dry flasks at room temperature until use.

EXAMPLE 4.3

Coating Petri Dishes with IL-3 20 ng per ml and IGF 20 ng per ml

Prepare 20 ml of 20 ng per ml IL-3 and 20 ng per ml IGF solution in PBS.
Fill every petri dish with 0.5-2.5 ml IL-3 and IGF solution.
Incubate at 37 degrees C. for 0.5 hours.
Collect the solution.
Wash flask twice in 10 ml PBS.
Keep dry flasks at room temperature until use.

5. In accordance with some applications of the present invention, serum preparation is carried out using the following protocol:
Serum can be obtained directly or prepared from plasma.

EXAMPLE 5.1

Preparation of Serum from Human Plasma

Take 100 ml of undiluted blood.
Spin at 1100 g (2500 rpm) for 10 min
Transfer the upper layer (plasma) to a new 50 ml tube.
To plasma diluted or undiluted 1:1 with PBS or Serum-free medium (e.g., X-VIVO 15™ and BIOTARGET-1™)
Add 25-75 ul (microliter) 0.8-0.24 M $CaCl_2\text{-}2H_2O$ for every 1 ml plasma.
Incubate for 0.5-3 hours at 37 degrees C.
Spin coagulated plasma 5 minutes at 2500 g.
Collect the serum in a new tube, avoiding clotting.
Aliquot collected serum and save at −20 degrees C. until use.
6. In accordance with some applications of the present invention, medium preparation is carried out using one or more of the following protocols:
Medium should typically contain 1-20% autologous serum and/or 1-20% conditioned medium.

EXAMPLE 6.1

Medium Additives for Generation, Activation, and Expansion of Multipotent Adult Stem/Progenitor Cells MASPC Medium can contain one or more additives, such as LIF, EPO, TPO, IGF, Insulin, IL-10, IL-3, IL-4, Alpha-1 Antitrypsin, Flt3-L, b-FGF, M-CSF, GM-CSF, TGF beta, TNF alpha, VEGF, estrogen, progesterone, prostaglandin, cortisone, cortisol, dexamethasone, or any other molecule from the steroid family, prolactin, an adrenocorticoid hormone, ACTH, glutamate, Ckit-L, CpG ODN, NO, Heparin, insulin, IFN alpha, IFN beta, or any other immunoregulatory agent, PDGF, thrombin, and/or Rosiglitazone in various concentrations, typically ranging from about 100 pg/ml to about 100 ug/ml (or molar equivalents).

EXAMPLE 6.2

Medium Additives for Generation of Lineage Specific Precursor/Progenitors (LSP)

Medium can contain one or more additives, such as LIF, EPO, IGF, b-FGF, M-CSF, GM-CSF, TGF alpha (TGFα), TGF beta (TGFβ), VEGF, BHA, BDNF, NGF, EGF, NT3, NT4/5, GDNF, S-100, CNTF, NGF3, CFN, ADMIF, estrogen, progesterone, prostaglandin, cortisone, cortisol, dexamethasone, or any other molecule from the steroid family, prolactin, an adrenocorticoid hormone, ACTH, glutamate, serotonin, acetylcholine, NO, retinoic acid (RA) or any other vitamin D derivative, Alpha-1 Antitrypsin, Heparin, insulin, forskolin, Simvastatin, MCDB-201, MCT-165, glatiramer acetate, IFN alpha, IFN beta or any other immunoregulatory agent sodium selenite, linoleic acid, ascorbic acid, transferrin, 5-azacytidine, PDGF, VEGF, cardiotrophin, and thrombinor Rosiglitazone in various concentrations, typically ranging from about 10 pg/ml to about 100 ug/ml (or molar equivalents).

Typically, but not necessarily, medium should be used within 10 days of its preparation date.

EXAMPLE 6.3

Growth Medium for Enhancement of DCP

Serum-free medium (e.g., X-VIVO 15™ and BIOTARGET-1™)
5-25 IU/ml Heparin
2.5-25 ng/ml Insulin
2.5-50 ng/ml IL-10
5-20 ng/ml IL-3
10-100 ng/ml IGF
5-50 ng/ml b-FGF
For some of the experiments described herein, media were prepared using combinations of two or more of the components listed in this example.

EXAMPLE 6.4

Growth Medium for Enhancement of DCP

Serum-free medium (e.g., X-VIVO 15™ and BIOTARGET-1™)
1-10% autologous serum
5-25 IU/ml Heparin
2.5-50 ng/ml IL-10
100-1000 IU/ml IL-4
50-250 ng/ml GM-CSF
0.5-20 ng/ml VEGF
2.5-50 ng/ml b-FGF
For some of the experiments described herein, media were prepared using combinations of two or more of the components listed in this example.

EXAMPLE 6.5

Growth Medium for Enhancement of DCP

Serum-free medium (e.g., X-VIVO 15™ and BIOTARGET-1™)
1-10% autologous serum
5-25 IU/ml Heparin
100-1000 IU/ml IL-4
50-250 ng/ml GM-CSF
10-100 ng/ml TGF beta
10-100 ng/ml TNF alpha
2-20 ng/ml VEGF
5-50 ng/ml b-FGF
For some of the experiments described herein, media were prepared using combinations of two or more of the components listed in this example.

EXAMPLE 6.6

Growth Medium for Enhancement of DCP

Serum-free medium (e.g., X-VIVO 15™ and BIOTARGET-1™)
1-10% autologous serum
5-25 IU/ml Heparin
100-1000 IU/ml IL-4
250-1000 ng/ml Alpha-1 Antitrypsin,
10-100 ng/ml TGF beta
10-100 ng/ml TNF alpha

For some of the experiments described herein, media were prepared using combinations of two or more of the components listed in this example.

EXAMPLE 6.7

Growth Medium for Enhancement of MASPC

Serum-free medium (e.g., X-VIVO 15™ and BIOTARGET-1™)
1-10% autologous serum
5 IU/ml Heparin
50-250 ng/ml IL-10
50-250 ng/ml Insulin
10-100 ng/ml IGF
10-100 ng/ml Flt3-L
5-50 ng/ml b-FGF
For some of the experiments described herein, media were prepared using combinations of two or more of the components listed in this example.

EXAMPLE 6.8

Growth Medium for Enhancement of MASPC

Serum-free medium (e.g., X-VIVO 15™ and BIOTARGET-1™)
5-20% autologous serum
5-25 IU/ml Heparin
50-250 ng/ml IL-10
50-250 IU/ml IL-4
250-1000 ng/ml Insulin
10-100 ng/ml IGF
10-100 ng/ml TNF alpha
For some of the experiments described herein, media were prepared using combinations of two or more of the components listed in this example.

EXAMPLE 6.9

Growth Medium for Enhancement of LSP-EPC

Serum-free medium (e.g., X-VIVO 15™ and BIOTARGET-1™)
5-20% autologous serum
5-25 IU/ml Heparin
50-250 ng/ml IL-10
50-250 IU/ml IL-4
50-250 ng/ml Insulin
10-100 ng/ml IGF
10-100 ng/ml b-FGF
2-20 ng/ml VEGF
For some of the experiments described herein, media were prepared using combinations of two or more of the components listed in this example.

EXAMPLE 6.10

Growth Medium for Enhancement of LSP-Tolerance Enhancing Cell Precursors (TECP)

Serum-free medium (e.g., X-VIVO 15™ and BIOTARGET-1™)
5-20% autologous serum
5-25 IU/ml Heparin
10-100 ng/ml TGF beta
50-250 ng/ml IL-10
10-100 ng/ml b-FGF
2-20 ng/ml VEGF
For some of the experiments described herein, media were prepared using combinations of two or more of the components listed in this example.

EXAMPLE 6.11

Growth Medium for Enhancement of LSP-anti Cancer Cell Precursors (aCCP)

Serum-free medium (e.g., X-VIVO 15™ and BIOTARGET-1™)
5-20% autologous serum
5-25 IU/ml Heparin
50-250 IU/ml IL-4
10-100 ng/ml b-FGF
2-20 ng/ml VEGF
5-50 ug/ml SCP-1 (or alternative Tumor associated antigens)
For some of the experiments described herein, media were prepared using combinations of two or more of the components listed in this example.

EXAMPLE 6.12

Growth Medium for Enhancement of LSP-anti Cancer Cell Precursors (aCCP)

Serum-free medium (e.g., X-VIVO 15™ and BIOTARGET-1™)
1-20% autologous serum
5-25 IU/ml Heparin
0.5-50 ng/ml IL-12
2.5-50 ng/ml IL-18
5-100 ng/ml IL-27
5-50 ug/ml SCP-1 (or alternative Tumor associated antigens)
For some of the experiments described herein, media were prepared using combinations of two or more of the components listed in this example.

EXAMPLE 6.13

Growth Medium for Enhancement of LSP-Engraftment Enhancing Cell Precursors (ECP)

Serum-free medium (e.g., X-VIVO 15™ and BIOTARGET-1™)
5-20% autologous serum
5-25 IU/ml Heparin
10-250 ng/ml IL-10
10-100 ng/ml TGF beta
2-20 ng/ml b-FGF
For some of the experiments described herein, media were prepared using combinations of two or more of the components listed in this example.

EXAMPLE 6.14

Growth Medium for Enhancement of Neuronal Cell Precursors (NCP)

Serum-free medium (e.g., X-VIVO 15™ and BIOTARGET-1™)
10% autologous serum
5-25 IU/ml Heparin 20 ng/ml b-FGF
50 ng/ml NGF
25 ng/ml BDNF
10-250 ng/ml IL-10
10-100 ng/ml TGF beta
10-100 ng/ml IGF
1-20 ug/ml insulin For some of the experiments described herein, media were prepared using combinations of two or more of the components listed in this example.

EXAMPLE 6.15

Growth Medium for Enhancement of Muscle Cell Precursors (MCP)

Serum-free medium (e.g., X-VIVO 15™)
10% autologous serum
20 ng/ml b-FGF
20 ng/ml IFN beta
5-25 IU/ml heparin.
10% MCDB-201
1-4% $H_2O_2$
2 ug/ml Insulin
2-20 ug/ml Transferin
10-50 ng/ml Sodium Selenite
1-50 nM Dexamethasone
0.4-10 ug/ml Linoleic acid
0.1 mM Ascorbic Acid For some of the experiments described herein, media were prepared using combinations of two or more of the components listed in this example.

7. In accordance with some applications of the present invention, conditioned medium preparation is carried out using the following procedure:

EXAMPLE 7.1

Preparation of 100 Ml Enriched Growth Medium Containing 1-20% Autologous Conditioned Medium Thaw 10 ml conditioned medium in an incubator.
When thawed, add it to culture medium using pipette.

8. In accordance with some applications of the present invention, culturing of cells to produce a DCP and/or activated MASPC is carried out using one or more of the following procedures:

EXAMPLE 8.1

Incubation of DCP

Incubate immature APC and/or DC at concentration of 0.5-10 million per ml for 2-24 hours at 37 degrees C., 5% CO2.
Collect all conditioned medium into tubes.
Spin at 300 g for 10 min, at room temperature.
Preserve the conditioned medium in new sterile containers.

EXAMPLE 8.2

Incubation of Cells Under Hypoxic Conditions

For some applications, increased expansion and/or activation may be obtained by exposure of the cell culture to oxygen starvation, e.g., 0.1-5% or 5-15% oxygen (hypoxia), for 2-12 hours or 12-96 hours. This is typically done one or more times, at different points during cell culturing.

Incubate immature cells at concentration of 1-10 million per ml in an oxygen-controlled incubator.
Set the oxygen pressure at 0.1%, and maintain it at this level for 48 hours.
Remove the cells from the incubator and examine the culture for viability using trypan blue.
Set the oxygen pressure of the incubator at 20%.
Re-insert the cells into the incubator and continue incubation for the rest of the period. This procedure can be repeated, for example, during the culture period and/or within 24, 48, or 72 hours before termination of the culture.

EXAMPLE 8.3

Incubation of DCP Under Hypoxic Conditions

Incubate immature APC and DC at concentration of 0.5-10 million cells per ml for 4-10 days in an oxygen-controlled incubator.
On days 1, 4, and 8 apply hypoxic condition by setting the oxygen pressure at 0.1%, and maintain it at this level for 24 hours.
Remove the cells from the incubator and examine the culture for viability using trypan blue.
Set the oxygen pressure of the incubator at 20%.
Re-insert the cells into the incubator and continue incubation for the rest of the period.

EXAMPLE 8.4

Harvesting of Adherent, and/or Detached, and/or Floating Cells

For some applications, increased expansion and differentiation of the cells may be achieved by re-seeding collected cells on new pre-coated dishes in culture medium.
Collect all conditioned medium and floating cells in tubes.
Spin at 300 g for 10 min, at room temperature.
Preserve the conditioned medium in new sterile containers.
Add the cells to all other collected cells from the culture dish.
Carefully wash the surface of tissue culture dishes by pipetting with cold PBS to detach adherent cells.
Collect the washed cells and add them to the tubes.
Add 5 ml of cold PBS.
Detach remaining adherent cells using gentle movements with cell scraper.
Collect the detached cells and add them to the tubes.
Optionally, add 5 ml EDTA to each flask and incubate at 37 degrees C. for 5 min
Collect the detached cells and add them to the tubes. Spin tubes for 5 minutes at 450 g, RT.
Completely discard the supernatant.
Re-suspend the pellets in fresh medium.
Count suspended cells, possibly in hemocytometer, assess viable cells using trypan blue.
Continue culturing the cells, and perform all other activities (e.g., medium refreshment, visual inspection, and/or flow cytometry), as appropriate, as described herein.

This procedure can be performed weekly during the culture period and/or within 24, 48, or 72 hours before termination of the culture.

EXAMPLE 8.5

Co-culture of DCP and Stem/Progenitor Cells with Multipotent Stem/Progenitor Cells (MASPC) in Order to Generate Activated MASPC For most applications, increased expansion and differentiation of MASPC may be achieved by co-culturing DCP and stem/progenitor cells as described herein below:

Count the harvested DCP cells and isolated stem/progenitor cells possibly in hemocytometer, assess viable cells using trypan blue.

Mix DCP and MASPC at ratios typically ranging from 1:5 to 1:50, for example, add 1 million DCP cells to 10 million isolated MASPC.

Incubate mixed cell population cells at concentration of 1.5-10 million cells per ml.

Continue growing and/or harvesting as appropriate, in accordance with procedures described herein.

Collect conditioned medium into 0.5 ml, 5 ml, 15 ml tubes or 50 ml tubes.

Spin collected conditioned medium at 450 g for 10 min, at room temperature.

Preserve the conditioned medium in new sterile containers.

EXAMPLE 8.6

Co-culture of Activated MASPC and TDC to Generate LSP

In accordance with some applications of the present invention, culturing of cells to produce a LSP is carried out using one or more of the following procedures:

Mix single cell suspension of TDC prepared in accordance with procedures described herein with MASPC at ratios typically ranging from 1:2 to 1:50, for example, add 1 million MASPC cells to 5 million TDC.

Continue growing and/or harvesting as appropriate, in accordance with procedures described herein.

9. In accordance with some applications of the present invention, extraction of tissue pieces for co-culture is carried out using one or more of the following procedures:

EXAMPLE 9.1

Extraction of Tissue Pieces for Co-culture

Dissection of autologous blood vessels (other non-human or human tissues may also be used):

Anesthetize the leg (or other area) from which the blood vessel will be sampled, using anesthetic reagents.

Using sterile scissors, cut the skin and expose the inner dermis.

Using a second set of sterile scissors, cut the dermis and expose the blood vessels.

Cut small pieces, 0.2-1 cm long, from the blood vessels, and place them in a container pre-filled with 50 ml cold culture growth medium (such as X-VIVO 15).

Using forceps and scissors, clean tissue sections.

Using forceps and scalpel, cut each blood vessel along its length, and expose the inner layer of endothelial cells.

Using forceps and scalpel, cut small pieces of up to 0.1 cm^2 from the tissue.

It is to be understood that whereas this technique is in accordance with some applications of the present invention, the scope of the present invention includes extracting a blood vessel from the patient as well. For example, an incision may be made over the saphenous vein, in order to facilitate dissection of a distal 1 cm portion of the vein. Tributary veins thereto are tied and transected. Distal and proximal ends of the 1 cm portion of the saphenous vein are tied, and the vein is harvested.

Use the dissected tissue for direct and/or indirect co-culturing with cells and/or to generate conditioned medium.

EXAMPLE 9.2

Antigen/Epitope Retrieval from Paraffin Embedded Target Tissue

Antigen/Epitope retrieval from paraffin embedded target tissue is performed using published or commercial methods.

EXAMPLE 9.3

Generation of Conditioned Medium

Lay dissected pieces in culture containers, for example in Petri dish, or 50 ml tubes.

Optionally, fill with cell culture medium containing 0.1-3 ug/ml or 3-100 ug/ml apoptotic reagent (such as valinomycin, etoposide or Staurosporine), until all pieces are covered.

Refresh culture medium every 2-4 days.

Collect this medium into 0.5 ml, 5 ml, 15 ml tubes or 50 ml tubes.

Spin collected conditioned medium at 450 g for 10 min, at room temperature. Collect conditioned medium in new sterile containers.

Continue growing and/or harvesting as appropriate, in accordance with procedures described herein.

EXAMPLE 9.4

Generation of Conditioned Medium

Conditioned medium is prepared as part of the culture step (e.g., culture of cells from a list of DCP, TDC, MASPC or co-culturing thereof).

At any step during and at the end of culture period, conditioned medium is collected.

Collect this medium into 15 ml tubes or 50 ml tubes.

Spin collected conditioned medium at 450 g for 10 min, at room temperature. Collect conditioned medium in new sterile containers.

10. In accordance with some applications of the present invention, co-culturing of tissue pieces or conditioned medium with DCP to specifically activate the DCP is carried out using one or more of the following protocols:

EXAMPLE 10.1

Direct Co-culturing of Tissue Pieces with DCP in Petri Dish

Lay dissected pieces in culture containers, for example in Petri dish.

Optionally, fill with cell culture medium containing 0.1-3 ug/ml or 3-100 ug/ml apoptotic reagent (such as valinomycin, etoposide or Staurosporine), until all pieces are covered.

Spin suspension of harvested DCP for 15 minutes at 450 g, 21 degrees C., pipette off supernatant.

Gently, mix cell pellet and re-suspend cells.

Re-suspend pellet to 0.5-10 million cells per ml.

Fill Petri dish with 3 ml enriched medium, and add the DCP suspension.

Incubate at 37 degrees C., 5% CO2 for 2-24 hours.

Collect culture medium containing floating, activated DCP, cells in tubes.

Carefully wash culture dish surface by pipetting with cold PBS to detach adherent cells.

Collect washed cells into the tubes.

Spin tubes for 5 minutes at 450 g, room temperature.

Re-suspend the pellets in culture medium.

Count suspended cells, possibly in hemocytometer, assess viable cells using trypan blue.

Continue growing and/or harvesting as appropriate, in accordance with procedures described herein.

EXAMPLE 10.2

Direct Co-culturing of Tissue Pieces with DCP and MASPC in Petri Dish

Lay dissected pieces in culture containers, for example in Petri dish.

Optionally, fill with cell culture medium containing 0.1-3 ug/ml or 3-100 ug/ml apoptotic reagent (such as valinomycin, etoposide or Staurosporine), until all pieces are covered.

Spin suspension of harvested DCP for 15 minutes at 450 g, 21 degrees C., pipette off supernatant.

Gently, mix cell pellet and re-suspend cells.

Re-suspend pellet to 0.5-10 million cells per ml.

Fill Petri dish with 3 ml enriched medium, and add the DCP suspension.

Incubate at 37 degrees C., 5% CO2 for 2-48 hours.

Collect culture medium containing floating, activated DCP, cells in tubes.

Carefully wash culture dish surface by pipetting with cold PBS to detach adherent cells.

Collect washed cells into the tubes.

Spin tubes for 5 minutes at 450 g, room temperature.

Re-suspend the pellets in fresh culture medium without apoptotic agents.

Add MASPC to the medium.

Count suspended cells, possibly in hemocytometer, assess viable cells using trypan blue.

Add cells at concentration of 0.5-10 million cells per ml.

Continue growing and/or harvesting as appropriate, in accordance with procedures described herein.

EXAMPLE 10.3

Culturing of Cells in the Presence of Conditioned Medium Derived from a Blood Vessel Culture Spin cells for 15 minutes at 500 g, 21 degrees C.

Discard the supernatant.

Gently mix cell pellet and re-suspend cells to 5-50 million/ml in autologous medium containing 1-20% autologous serum and/or 1-20% conditioned medium.

Seed cells at concentration of 1-10 million cells per ml.

Incubate flasks at 37 degrees C., 5% CO2.

After first three days of culture, non-adherent cells can be removed from the culture.

EXAMPLE 10.4

Direct Co-culturing of Autologous Dissected Blood Vessel and MASPC Cells

Lay dissected tissue pieces in culture dishes.

Add MASPC and TDC to the culture.

Every 2-4 days, conditioned medium can be collected and preserved in accordance with procedures described herein.

Refresh culture medium with appropriate culture medium prepared in accordance with procedures described herein.

Using forceps, take out tissue pieces after 2-4 days of co-culture.

Continue growing and harvesting as appropriate, in accordance with procedures described herein.

11. In accordance with some applications of the present invention, refreshing of the medium in ongoing growing cultures is carried out using the following protocol:

Refreshing of the medium in ongoing growing cultures should be done every 2-4 days.

EXAMPLE 11.1

Refreshing of Growth Medium in Cultures

Collect medium containing non-adherent cells in 0.5 ml, 5 ml, 50 ml tubes.

Fill every culture dish with fresh growth medium enriched with conditioned medium. Typically, for a T75 flask, fill 10 ml fresh growth medium.

Spin tubes for 10 minutes at 450 g, RT; pipette off supernatant completely.

Gently mix cell pellet and re-suspend cells in 10 ml fresh growth medium enriched with condition medium.

Return cell suspension to the culture dish.

12. In accordance with some applications of the present invention, harvesting of the cellular product is carried out using the following protocol:

EXAMPLE 12.1

Harvesting of LSP

Collect culture medium containing floating cells in tubes.

Carefully wash flask surface by pipetting with cold PBS to detach adherent cells.

Collect washed cells into the tubes.

Add 5 ml of cold PBS.

Detach remaining adherent cells using gentle movements with cell scraper.

Collect the detached cells and add them to the tubes.

Optionally, add 5 ml EDTA to each flask and incubate at 37 degrees C. for 5 minutes.

Collect the detached cells and add them to the tubes

Spin tubes for 5 minutes at 450 g, room temperature.

Re-suspend the pellets in 2-5 ml PBS.

Count suspended cells, possibly in hemocytometer, assess viable cells using trypan blue.

13. In accordance with some applications of the present invention, cell preservation is carried out using one or more of the following protocols:

Cellular product can be kept in preservation medium or frozen in freezing buffer until use for transplantation into a patient and/or for diagnostics and/or for research. For some applications, the cell products are frozen in buffy coat.

EXAMPLE 13.1

Cryopreservation of Cells (DC and or MASPC and/or LSP)

Prepare a serum-free freezing buffer containing 10% DMSO, such as Serum-Free Cell Freezing Medium for the cryopreservation of mammalian cells (05-065-1, Biological Industries, Israel) or alternative.

Count suspended cells, possibly in hemocytometer, assess viable cells using trypan blue.

Do not preserve cells if the viability is less than 70%.

Suspend cellular product in freezing buffer and freeze in −80° C. or in liquid nitrogen.

EXAMPLE 13.2

Cryopreservation of Cells (DC and or MASPC and/or LSP)

Prepare freezing buffer containing 90% human autologous serum and 10% DMSO.

Count suspended cells, possibly in hemocytometer, assess viable cells using trypan blue.

Do not preserve cells if the viability is less than 70%.

Suspend cellular product in freezing buffer and freeze in −80° C. or in liquid nitrogen.

EXAMPLE 13.3

Short-period Preservation of Cellular Product

Prepare preservation medium including growth medium containing 1-20% autologous serum, with few or no other additives.

Count suspended cells, possibly in hemocytometer, assess viable cells using trypan blue.

Do not preserve cells if the viability is less than 70%.

Maintain preservation medium with cellular product at 2-12 degrees C.

14. In accordance with some applications of the present invention, conditioned medium collection and preservation is carried out using the following protocol:

EXAMPLE 14

Conditioned Medium can be Kept Until Use for Growth Medium Preparation or for Therapeutic Application Conditioned medium should be collected under sterile conditions.

Spin collected conditioned medium for 10 min at 450 g, 21 degrees C.

Collect supernatant in new sterile containers.

Filter supernatant through a 22 um (micrometer) membrane.

Aliquot conditioned medium to 0.5-10 ml sterile tubes and/or 50 ml sterile tubes, pre-marked with donor details.

Keep at (−20)-(−80) degrees C. until use.

15. In accordance with some applications of the present invention, FACS staining is carried out using the following protocol:

EXAMPLE 15

Cell Staining Protocol for FACS Analysis can be Done Using Common Protocols Such as "FACS Staining Protocols" I and II

EXAMPLE 15.1

Staining of Endothelial LSP Enriched Population

FACS staining protocol with antibodies against:

| Tube No. | Staining | Aim of staining |
|---|---|---|
| 1. | Cells | Un-stained control |
| 2. | CD45-FITC (IgG1) | Single staining for PMT |
| 3. | CD45-PE (IgG1) | and compensation settings |
| 4. | CD45-APC (IgG1) | |
| 5. | mIgG1-FITC<br>mIgG1-PE<br>mIgG1-APC | Isotype control |
| 6. | CD184 (CXCR4)-FITC (IgG1)<br>CD144-PE (IgG2a)<br>CD34-APC (IgG1) | Specific staining |
| 7. | Ulex lectin-FITC<br>Ac-LDL-Dil | Specific staining |
| 8. | CD31-FITC (IgG1)<br>CD202b-PE (IgG1) | Specific staining |
| 9. | CD141-FITC (IgG1)<br>CD303 or CD304-PE (IgG1) | Specific staining |
| 10. | CD8-FITC (IgG1)<br>CD56-PE (IgG1) | Specific staining |
| 11. | CD31-FITC (IgG1)<br>VEGFR1-PE (IgG1) | |
| 12. | CD309-FITC (IgG1)<br>CD202b-PE (IgG1) | |
| 13. | CD220-FITC (IgG1)<br>CD221-PE (IgG1) | Specific staining |

16. In accordance with some applications of the present invention, immunohistochemistry staining (IHC) is carried out using the following protocol:

EXAMPLE 16

Cell Staining Protocol for IHC and/or Immunoflouresence Analysis can be Done Using Common Protocols such as "Immunofluorescence Double Staining Protocol—Parallel Approach"

EXAMPLE 16.1

IHC Staining Protocol for Endothelial LSP

| Slide No. | Staining | Aim of staining |
|---|---|---|
| 1. | mIgG1-FITC | Isotype control |
| 2. | mIgG1-PE | Isotype control |
| 3. | CD144-FITC | Specific Staining |
| 4. | CXCR4-PE | Specific Staining |
| 5. | Ulex-Lectin-FITC<br>Ac-LDL-Dil | Specific Staining |

17. In accordance with some applications of the present invention, a tube formation assay is carried out using the following protocol:

EXAMPLE 17

Tube Formation was Tested Using the ECM625 (CHEMICON®) in vitro Angiogenesis Assay Kit.

Angiogenic pattern and vascular tube formation was numerically scored as described by Porat Y. et al. 2006 (Br J. Haematol. 2006; 135:703-714).
18. In accordance with some applications of the present invention, secretion of cytokines from harvested cells is assessed using the following starvation assay protocol:

EXAMPLE 18

Culture 0.5-1 Million Cells per ml Overnight in 24 Well Plates in Serum-free Medium (e.g., X-VIVO 15)

Collect starvation assay supernatant (SAS) and spin at 450 g for 5 minutes.
Transfer supernatant to an eppendorf tube and freeze at −80 degrees C. until ready to test cytokine secretion.

EXAMPLE 18.1

Cytokine Antibody Array

Detection of a panel of secreted cytokines is done using commercially semi-quantitative kits such as RayBio® "Human Angiogenesis Antibody Array 1" (Cat# AAH-ANG-1) and/or RAYBIO® "Human Growth Factor Antibody Array 1" (Cat# AAH-GF-1) and/or Milliplex Human Cytokine/Chemokine Immunoassay (Cat.# MPXHCYTO-60K-07). In accordance with some applications of the present invention, DCP capability of phagocytosis and antigen presentation is assessed using the following protocol:
Semi-quantitative detection of phagocytosis of stained particles is done using a commercial procedure such as "CYTOSELECT™ 96-Well Phagocytosis Assay" (Cell Biolabs cat. CBA-224)
19. In accordance with some applications of the present invention, stem and progenitor cells capability to form cell colonies is assessed using the following protocol:

EXAMPLE 19

Detection of a Panel of Colony Types is Done Using a Commercial Procedure Such as "Procedure for the Human Colony Forming Unit Cell (CFU; CFC) Assay Using Methylcellulose-based Media" (R&D System Inc. Cat. # HSC001, HSC002, HSC003, HSC004 and HSC005).

20. In accordance with some applications of the present invention, stem and progenitor cells migration capability is assessed using the following protocol:

EXAMPLE 20

Quantitative Detection of Migratory Cells is Done Using a Commercial Procedure Such as "A quantitative Cell Migration Assay Using THINCERT™ Cell Culture Inserts" (Greiner Bio-One).

21. In accordance with some applications of the present invention, stem and progenitor cells engraftment capability in a tissue is assessed using the following protocol:

EXAMPLE 21

Detection of Metalloproteinases-9 (MMP-9) is Done Using a Commercial Procedure Such as "SENSOLYTE PLUS™ 520 MMP-9 Assay Kit *Fluorimetric and Enhanced Selectivity*" (AnaSpec, Inc).

Cytotoxic Lymphocyte Reaction Assay (CTL)
In accordance with some applications of the present invention, a cytotoxic lymphocyte reaction assay (CTL) is carried out using the following protocol (typically, the CTL is conducted to assess the cytotoxic reaction of the LSP-aCCP):
Step 1: Preparation of Target Cells for Targeting by LSP-aCCP in the CTL
Collect Target Cells (K562 (cell line) or PBMC from unrelated donor or any other cells) from flask into 50 ml tube.
Wash the flask with 5-10 ml PBS and add to the 50 ml tube.
Spin cells 7 min, 300 g, 21 degrees C., accelerate 9, brake 5.
Discard supernatant and gently resuspend cell pellet.
Add 10 ml PBS by washing tube and gently resuspend cells (possibly by pipettation).
Spin cells 7 min, 300 g, 21 degrees C., accelerate 9, brake 5.
Discard supernatant and gently resuspend cell pellet.
Add 3-5 ml PBS (according to cell pellet size).
Take samples of cells for counting in trypan blue.
Calculate the volume for 3 million target cells.
Transfer 3 million target cells into 15 ml tube.
Spin cells 7 min 300 g, 21 degrees C., accelerate 9, brake 5.
Discard supernatant and gently resuspend cell pellet.
Add 1 ml PBS.
Gently resuspend cells by repeat pipetting. Avoid generating bubbles.
Prepare fresh intermediate dilution of 50 uM (microMolar) CFSE (1:100 from the 5 mM stock (cat#65-0850-84—eBioscience, preserved at −20 degrees C.)).
Add 5 ul of diluted CFSE to the cells (final concentration 0.25 uM).
Incubate tubes 15 minutes at room temperature protected from light.
After incubation, add 3 ml CTL medium (RPMI+15% FCS) per 3 million cells.
(Note: Serum is needed to stop the CFSE binding reaction; use at least 10% serum in the CTL Medium.)
Spin cells 7 min 300 g, 21 degrees C., accelerate 9, brake 5.
Discard supernatant and gently resuspend cell pellet.
Add 2-3 ml CTL medium by washing tube and gently resuspend cells (possibly by pipettation).
Spin cells 7 min 300 g, 21 degrees C., accelerate 9, brake 5.
Discard supernatant and gently resuspend cell pellet.
Add 2-3 ml CTL medium by washing tube and gently resuspend cells (possibly by pipettation).
Incubate cells in a loosely capped tube at 37 degrees C. in CO2 for 30-60 min
Spin cells 7 min 300 g, 21 degrees C., accelerate 9, brake 5.
Discard supernatant and gently resuspend cell pellet.
Add 2 ml PBS.
Spin cells 7 min 300 g, 21 degrees C., accelerate 9, brake 5.
Discard supernatant and gently resuspend cell pellet.
Calculate needed volume of CTL medium to get a target cell concentration of 0.5 million cells/ml (so that aliquot of 100 ul contains 50,000 stained target cells per tube).

Resuspend the cells in the CTL medium.
Step 2: Mixing Target and Effectors Cells
Determine the total cell concentration of effectors cells of the LSP-aCCP.
Add 100 ul of target cells (K562) to all experimental FACS tubes.
In this test several target/effectors ratios such as 1:0,1:0.5, 1:1, 1:5, 1:10, 1:50, 1:100 will be examined.
Add Effectors Cells suspended in CTL Medium, up to 100 ul per tubes.
Adjust the volume of each sample 400 ul.
Incubate 4 hours in 37 degrees C. 5% CO2.
20 min before the incubation is over prepare control tubes:
Tube of viable target cells (prepared from step 1) stained with CFSE+effectors cells (1:10) dually stained with 7-AAD.
Tube of viable CFSE stained target cells dually stained with 7-AAD.
Tube of killed CFSE stained Target Cells dually stained with 7-AAD.
Note: calibrate all control tubes to t=0.
Use 0.1 million target cells for each control.
Adjust the volume of each control to 200 ul.
Add 5 ul 7-AAD to the sample tubes.
Incubate on ice for 15 min protected from light.
Set up the FACS gating and compensation based on control cells.
Step 3: Preparation of Dead Cells Control:
Add 5 ul of non-ionic surfactant TRITON™ X-100 100% or NP-40 to the CFSE stained target cells (from step 1).
Incubate 5 min in RT.
Add 3 ml PBS.
Spin cells 7 min, 300 g, 21 degrees C., accelerate 9, brake 5.
Resuspend the cells in 200 ul CTL Medium.
CTL Medium Preparation (Good for K562 Growth):
Prepare CTL medium according to the table below:

| CTL Medium | | |
|---|---|---|
| Component | Final conc. | Volume |
| Volume ml | | 500 |
| RPMI (ml) | 83% | 417 |
| FCS (ml) | 15% | 75 ml |
| L-Glutamin (ml) | 1% | 5 ml |
| Antibiotics (Strep + Pen) (ml) | 1% | 5 ml |

EXPERIMENTAL DATA

The experiments described hereinbelow were performed by the inventor in accordance with some applications of the present invention and using the techniques described hereinabove.

EXPERIMENTAL EXAMPLE 1

Isolation of DCP

In this set of experiments, directing cell populations (DCP), having an enriched population of dendritic cells (DC), were generated from cord blood mononuclear cells (CBMC). First, cord blood was extracted from six umbilical cord blood donations for use in six respective experiments. The CBMC was obtained by preliminary processing of the cord blood by use of FICOLL™ density gradient, in accordance with the protocols described hereinabove with reference to Example 1.3, extraction of CBMC. Plasmacytoid and myeloid dendritic cells were then isolated from the CBMC using cellular markers-based procedures in accordance with protocols described hereinabove with reference to Examples 2.7.1, 3.1, and 3.4. It is possible (although not included in this experimental example) to isolate the dendritic cells from the CBMC using cellular markers-based procedures in accordance with protocols described hereinabove with reference to Examples 3.2, 3.3, 3.5, or 3.6. The obtained DCP-enriched population of cells was further sorted by immunostaining and FACS analysis based on cell surface antigens in accordance with protocols described hereinabove with reference to Example 15, in order to determine enrichment of the DCP. Results of the enrichment include an increased percentage of the cells expressing the markers CD141 and/or CD303/CD304. Data collected from the 6 independent experiments show an increased percentage of DC cells expressing the markers CD141 and/or CD303/CD304, from 4.0% in the CBMC to 47.9% in the DCP; the percentage of CD141 increased from 0.2+/−0.0% in the CBMC to 2.6+/−0.5% in the DPC, $p<0.01$; and the percentage of cells expressing CD303/CD304 increased from 3.8+/−1.0% in the CBMC to 45.3+/−6.7% in the DPC, $p<0.01$.

Table I is a table representing the enrichment of myeloid DC and plasmacytoids DC in the DCP compared to the CBMC following the procedures described hereinabove. As shown, percentages of CD141 (myeloid DC) and CD303/CD304 (plasmacytoids DC) were increased in the DCP compared to the CBMC, from which the DCP was generated. The Enrichment Factor shown in Table I was determined by dividing the percentage of cells having a given characteristic in the DCP by the percentage of cells having that characteristic in the CBMC [enrichment=% in DCP/% in CBMC].

TABLE I

| Exp No. | % Cells expressing CD141 | | | % Cells expressing CD303/CD304 | | |
|---|---|---|---|---|---|---|
| | CBMC | DCP | Enrichment Factor | CBMC | DCP | Enrichment Factor |
| 1 | 0.2 | 4.0 | 20.0 | 5.4 | 40.8 | 7.6 |
| 2 | 0.1 | 1.5 | 15.0 | 8.4 | 34.0 | 4.0 |
| 3 | 0.1 | 3.1 | 31.0 | 1.9 | 39.8 | 20.9 |
| 4 | 0.3 | 2.8 | 9.3 | 2.0 | 40.2 | 20.1 |
| 5 | 0.1 | 3.3 | 33.0 | 1.1 | NA | NA |
| 6 | 0.3 | 1.0 | 3.3 | 4.0 | 71.6 | 17.9 |
| average | 0.2 | 2.6 | 18.6 | 3.8 | 45.3 | 14.1 |
| SE | 0.04 | 0.5 | 4.8 | 0.95 | 0.5 | 3.5 |
| | | $p<0.01$ | | | $p<0.01$ | |

EXPERIMENTAL EXAMPLE 2

Activation of DCP

In this set of experiments, DCPs, having an enriched population of dendritic cells (DC), were generated from CBMC, as described in Experimental Example 1. Plasmacytoid and myeloid dendritic cells (DC) were then separated from the CBMC by use of a cellular markers-based procedure in accordance with protocols described hereinabove with reference to enrichment of DC. The obtained DCP was further activated by incubation of the DCP in a medium containing at least 10% autologous serum, 5 IU/ml Heparin with or without 20-50 ng/ml IL-10, and 1-20 ng/ml VEGF for 0.5 hours to 3 days in accordance with protocols described hereinabove with reference to Examples 5.1, 6.4, and 8.1. It is possible (although not included in this experimental example) to activate dendritic cells in accordance with protocols described hereinabove with reference to Examples 6.3, 6.5, 8.2, or 8.3. The DCP was sorted by immunostaining and FACS analysis based on cell surface antigens in order to determine the activation of the DCP. Activation of the DCs was determined by increased percentages of CD141 positive cells within the population and increased intensity of CD141 in the CD141 expressing cells.

Data collected from 6 independent experiments show that the percentages of CD141-expressing cells rose from 2.6+/−0.5% in the freshly isolated population to 8.6+/−2.1% in the post activated population p<0.05.

See Table II for individual results, showing that the activated DCP population expressed increased intensity of CD141 following 3 hours activation:

TABLE II

DCP Expressing increased intensity of CD141

| Sample No. | DCP at Time = 0 | DCP after Time = 3-4 hours | Enrichment factor |
|---|---|---|---|
| 1 | 4.0 | 9.3 | 2.3 |
| 2 | 1.5 | 2.7 | 1.8 |
| 3 | 3.1 | 15.3 | 4.9 |
| 4 | 2.8 | 6.6 | 2.4 |
| 5 | 3.3 | 16.0 | 4.8 |
| 6 | 1.0 | 1.8 | 1.8 |
| Avg | 2.6 | 8.6 | 3.0 |
| SE | 0.2 | 2.1 | 0.6 |
| P |  | <0.01 |  |

EXPERIMENTAL EXAMPLE 3

Enrichment of TDC-derived MASPC

In this set of experiments, a population of TDC was isolated from the CBMC and enriched by depletion of CD8 and CD56-expressing cells as described hereinabove with reference to the method, "Isolation of Stem and Progenitor cells." First, cord blood samples were collected from seven umbilical cord blood donations for use in seven respective experiments. The CBMC were isolated from the umbilical cord blood samples by use of a FICOLL™ density gradient, in the manner described in Experimental Example 1. The desired TDC were then generated from the same CBMC from which the DCPs were isolated and enriched by binding of specific antibodies to undesired cell populations expressing CD8 and CD56 (T cells and NK cells respectively), and these cells were subsequently removed in accordance with protocols described hereinabove with reference to Example 2.6.

It is possible (although not included in this experimental example) to work in accordance with protocols described hereinabove with reference to Example 2.4.

Data collected from the 7 independent experiments show reduced percentage of TDC expressing the markers CD8 and CD56 in the TDC in comparison to their percentage in original CBMC; the percentage of CD8 decreased from 16.2+/−2.8% in the CBMC to 1.8+/−0.6% in the TDC, p<0.05; the percentage of CD56 decreased from 10.2+/−2.1% in the CBMC to 4.1+/−1.4% in the TDC, p<0.05. In parallel, the percentages of TDC expressing the hematopoietic stem/progenitor marker CD34 was 2.4 times enriched in comparison to their percentage in original CBMC; In six out of seven experiments the percentage of CD34 increased as a result of the depletion of CD8 and CD56-expressing cells. On average, the percentage of cells expressing CD34 increased from 1.0+/−0.3% in the CBMC to 1.7+/−0.5% in the TDC. TDC of more than 0.9% CD34 may be used as raw material in the process for generating the composition of matter (COM) of an LSP of EPC-Rich MASPC, as described in the present patent application.

Six umbilical cord blood samples provided the samples, respectively, for 6 out of 7 of these experiments. In these 6 out of 7 experiments each of the TDC and DCP were obtained from the same cord respective blood sample.

Table III is a table representing the enrichment of the TDC, achieved by depletion of CD8 and CD56-expressing cells in accordance with the procedures described hereinabove. As shown, percentages of CD8 (T cells) and CD56 (NK cells) were decreased and the percentage of CD34 increased in the TDC compared to the CBMC, from which the TDC was obtained. Enrichment in this set of experiments results from the depletion of selected populations of cells from the TDC. The Enrichment Factor shown in Table III was determined by dividing the percentage of cells having a given characteristic in the TDC by the percentage of cells having that characteristic in the CBMC [Enrichment=% in TDC/% in CBMC].

TABLE III

| | % Cells expressing CD8 | | | % Cells expressing CD56 | | | % Cells expressing CD34 | | |
|---|---|---|---|---|---|---|---|---|---|
| Exp No. | CBMC | RDC | Enrichment Factor | CBMC | TDC | Enrichment Factor | CBMC | TDC | Enrichment Factor |
| 1 | 7.7 | 1.6 | 4.8 | 6.0 | 3.1 | 1.9 | 0.2 | 0.9 | 4.5 |
| 2 | 11.7 | 2.6 | 4.5 | 7.3 | 7.2 | 1.0 | 0.8 | 3.2 | 4.0 |
| 3 | 18.1 | 0.2 | 90.5 | 9.2 | 0.4 | 23.0 | 0.3 | 0.9 | 3.0 |
| 4 | 27.3 | 1.5 | 18.2 | 21.8 | 2.3 | 9.5 | 0.6 | 1.2 | 2.0 |
| 5 | 8.00 | 1.2 | 6.7 | 6.80 | 2.4 | 2.8 | 1.9 | 0.6 | 0.3 |
| 6 | 22.6 | 1.1 | 20.5 | 13.4 | 11.0 | 1.2 | 0.9 | 1.5 | 1.7 |
| 7 | 18.3 | 4.3 | 4.3 | 7.1 | 2.1 | 3.4 | 2.5 | 3.4 | 1.4 |
| Avg | 16.2 | 1.8 | 21.4 | 10.2 | 4.1 | 6.1 | 1.0 | 1.7 | 2.4 |
| SE | 0.04 | 0.5 | 4.8 | 0.95 | 0.5 | 3.5 | 0.3 | 0.5 | 0.6 |
| | | P < 0.05 | | | P < 0.05 | | | | |

EXPERIMENTAL EXAMPLE 3.1

Depletion of Immature Red Blood Cells (imRBC)

In this set of experiments, a population of TDC was isolated from the CBMC and enriched by depletion of CD71-expressing cells, as described hereinabove with reference to Experimental Example 3. First, cord blood samples were collected from six umbilical cord donations for use in six respective experiments. The desired TDC were then generated from the CBMC and enriched by binding of specific antibodies to undesired cell populations expressing CD71 (immature Red Blood Cells (imRBC)), and these cells were subsequently removed in accordance with protocols described hereinabove with reference to Example 2.7 (Examples 2.7.1 and 2.7.2).

It is to be noted that it is possible (although not included in this experimental example) to work in accordance with protocols described hereinabove with reference to Example 2.4.

Data collected from the 6 independent experiments show reduced percentage of TDC expressing the markers CD71 in the TDC in comparison to their percentage in original CBMC; the percentage of CD71 decreased from 31.2+1-13.2% in the CBMC to 1.9+/−0.4% in the TDC.

EXPERIMENTAL EXAMPLE 4

Characterization of LSP of EPC-Rich MASPC—Morphological Analysis

In this set of experiments, an activated DCP was co-cultured with TDC in order to generate a population of lineage-specific precursors (LSP). The LSP generated in this set of experiments was an endothelial progenitor cell (EPC)-rich MASPC. First, a DCP was generated from human CBMC using the protocols described hereinabove in Experimental Examples 1 and 2. The isolated DCP was then maintained and activated in a medium for enhancement of DCP using the protocols described hereinabove in Experimental Example 2. The activated DCP was then co-cultured with TDC. Co-cultured cells were maintained in a medium containing at least (a) 5% autologous serum, (b) 5 IU/ml Heparin, and (c) 2-50 ng/ml IL-10 and/or 1-20 ng/ml VEGF. The medium was changed every 2-3 days, in accordance with protocols described hereinabove with reference to co-culturing of activated MASPC and TDC to generate LSP in accordance with protocols described hereinabove with reference to Examples 6.9 and 8.5. For some applications, neither IL-10 nor VEGF is included in the medium.

It is possible (although not included in this experimental example) to work in accordance with protocols described hereinabove with reference to Examples 6.7, 6.8, and 8.6.

The co-cultured activated DCP and TDC were plated on either serum- or plasma-coated plastic tissue culture plates. Cells were maintained in a medium containing at least (a) 10% autologous serum, (b) 5 IU/ml Heparin, and (c) 20-50 ng/ml IL-10 and/or 1-20 ng/ml VEGF. The medium was changed every 2-3 days. Other experimental data show that the cells were maintained in a medium containing at least 10% autologous serum, 5-25 IU/ml Heparin with or without 1-50 ng/ml IL-10, and 1-20 ng/ml VEGF (data not shown).

Reference is made to FIG. 1.

FIG. 1 is a representative photomicrograph of an endothelial progenitor cells (EPC)-rich multipotent adult stem/progenitor cells (MASPC) population, generated in accordance with some applications of the present invention. FIG. 1 shows the morphology of an endothelial progenitor cell (EPC) population generated by the co-culturing of activated human-CBMC-derived DCP and TDC as described hereinabove. As shown, elongated and spindle-shaped cells are typically observed in cultures of EPC-rich MASPC.

EXPERIMENTAL EXAMPLE 5

Characterization of LSP of EPC-Rich MASPC—Cell Yields, Surface Markers, and Physiological Activity In this set of experiments, an LSP of EPC-rich MASPC, was generated from the co-culturing of a human-CBMC-derived DCP together with TDC, as described hereinabove with reference to Experimental Examples 1, 2, 3, and 4. Co-cultured cells were maintained in a medium containing at least (a) 5% autologous serum, (b) 5 IU/ml Heparin, and (c) 2-50 ng/ml IL-10 and/or 1-20 ng/ml VEGF. The medium was changed every 2-3 days. For some applications, neither IL-10 nor VEGF is included in the medium.

The presence of DCP, MASPC and EPC in the culture was then assessed on day 1-4 of culturing, and was determined by FACS analysis by co-staining with FITC-labeled antibody against Ulex lectin and 1,1'-dioctadecyl-3,3,3',3'-tetramethyl-indocarbocyanine perchlorate labeled Acetylated Low Density Lipoprotein (Dil-Ac-LDL) Ac-LDL. FACS staining was performed in accordance with protocols described hereinabove with reference to Example 15.

Table IV-I is a table representing average flow cytometry immunostaining results obtained from seven independent experiments which were conducted in accordance with the procedures described hereinabove after 1-day culture. As shown in Table IV-I, co-culturing of DCP and TDC for 1 day typically yields an EPC-rich MASPC of 0.8+/−0.3 million cells per 1 ml blood (78.6+/−28 2 million cells per 100 ml cord blood) having at least 80% viability (98.7% as shown in the table), at least 0.2% CD141 (0.8%, as shown in the table), at least 2.5% CD303/CD304 (10.5%, as shown in the table), at least 2.5% hematopoietic stem/progenitor cells co-expressing CD34 and D184 (4.2%, as shown in the table) and at least 2.5% EPCs co-expressing Ulex lectin and uptake of Ac-LDL (10.9%, as shown in the table).

Table IV-II is a table showing average flow cytometry immunostaining results obtained from five independent experiments which were conducted in accordance with the procedures described hereinabove after 3-day culture. As shown in Table IV-II, co-culturing of DCP and TDC for 3 days typically yields an EPC-rich MASPC of 42.0+/−8.0 million cells per 100 ml cord blood having at least 80% viability (99.4% as shown in the table), at least 0.1% CD141 (0.3%, as shown in the table), at least 2.5% CD303/CD304 (7.4%, as shown in the table), at least 1.5% hematopoietic stem/progenitor cells co-expressing CD34 and D184 (6.9%, as shown in the table) and at least 2.5% EPCs co-expressing Ulex lectin and uptake of Ac-LDL (19.2%, as shown in the table).

TABLE IV-I

| Results after 1-day culture | | |
|---|---|---|
| Number experiments N = 7 | Average | SE |
| No. of cells(×10^6)/100 ml Cord Blood | 78.6 | 28.2 |
| % Viability | 98.7 | 0.3 |
| % DCP expressing CD141 in the LSP of EPC-Rich MASPC | 0.8 | 0.4 |
| % DCP expressing CD303/CD304 in the LSP of EPC-Rich MASPC | 10.5 | 2.5 |
| % MASPC co-expressing CD34 and CD184[+] in the LSP of EPC-Rich MASPC | 4.2 | 0.5 |
| % EPCs co-expressing Ac-LDL Uptake and Ulex lectin in the LSP of EPC-Rich MASPC | 10.9 | 2.0 |

TABLE IV-II

Results after 3-day culture

| Number experiments N = 5 | Average | SE |
|---|---|---|
| No. of cells(×10^6)/100 ml Cord Blood | 42.0 | 8.0 |
| Viability | 99.4 | 0.3 |
| DCP expressing CD141 in the LSP of EPC-Rich MASPC | 0.3 | 0.2 |
| DCP expressing CD303/CD304 in the LSP of EPC-Rich MASPC | 7.4 | 1.9 |
| MASPC co-expressing CD34 and CD184+ in the LSP of EPC-Rich MASPC | 8.3 | 1.9 |
| EPCs co-expressing Ac-LDL Uptake and Ulex lectin in the LSP of EPC-Rich MASPC | 19.2 | 5.7 |

EXPERIMENTAL EXAMPLE 6

Characterization of LSP of EPC-Rich MASPC—Additional Surface Marker Combinations In this set of experiments, an LSP of EPC-rich MASPC, was generated from the co-culturing of an activated human-CBMC-derived DCP together with TDC, as described hereinabove with reference to Experimental Examples 1, 2, 3, and 4. Co-cultured cells were maintained in a medium containing at least (a) 5% autologous serum, (b) 5 IU/ml Heparin, and (c) 2-50 ng/ml IL-10 and/or 1-20 ng/ml VEGF. The medium was changed every 2-3 days. For some applications, neither IL-10 nor VEGF is included in the medium.

The presence of EPC in the culture was then assessed on day 1-4 of culturing, and was determined by FACS analysis by co-staining with CD31 (PECAM-1) and VEGFR1 (vascular endothelial growth factor receptor 1). Additional staining was conducted to identify cells co-expressing CD309 (VEGFR2, KDR) and CD202b (Tie-2) as well as by co-staining with FITC-labeled antibody against Ulex lectin and Dil-Ac-LD uptake.

Table V-I is a table representing average flow cytometry immunostaining obtained from 7 independent experiments which were conducted in accordance with the procedures described hereinabove after 1-day culture with reference to Experimental Examples 1, 2, 3, and 4 and FACS staining protocol (Example 15).

Co-culturing of activated DCP and TDC for 1 day typically yields an LSP of EPC-rich MASPC having at least 5% of cells co-expressing Ac-LDL Uptake & Ulex lectin (on average, the percentage of cells co-expressing Ac-LDL Uptake & Ulex lectin was 10.9+/−2.0%), and at least 2.0% of cells co-expressing CD309 (VEGFR2, KDR) and CD202b (Tie-2), (on average, the percentage of cells co-expressing CD309 and CD202b was 5.6+/−1.2%), and at least 5% of cells co-expressing CD31 and VEGFR1 (on average, the percentage of cells co-expressing CD31 and VEGFR1 was 35.1+/−3.9%).

Table V-II is a table representing average flow cytometry immunostaining obtained from 5 independent experiments which were conducted in accordance with the procedures described hereinabove after 3-day culture with reference to Experimental Examples 1, 2, 3, and 4 and FACS staining protocol (Example 15).

Co-culturing of activated DCP and TDC for 3 days typically yields an LSP of EPC-rich MASPC having at least 5% of cells co-expressing Ac-LDL Uptake & Ulex lectin (on average, the percentage of cells co-expressing Ac-LDL Uptake & Ulex lectin was 19.2+/−5.7%), and at least 0.5% of cells co-expressing CD309 (VEGFR2, KDR) and CD202b (Tie-2) (on average, the percentage of cells co-expressing CD309 and CD202b was 5.9+/−2.8%), and at least 5% of cells co-expressing CD31 and VEGFR1 (on average, the percentage of cells co-expressing CD31 and VEGFR1 was 27.0+/−5.0%).

TABLE V-I

% Cells in the LSP of EPC-Rich MASPC - additional surface marker combinations - Results of Individual samples after 1-day culture

| Sample No. | EPCs co-expressing Ac-LDL Uptake & Ulex lectin | EPCs co-expressing CD309 & CD202B | EPCs co-expressing CD31 & VEGFR1 |
|---|---|---|---|
| 1 | 12.7 | 2.7 | 36.6 |
| 2 | 5.8 | 4.8 | 33.6 |
| 3 | 14.0 | 6.9 | 27.8 |
| 4 | 10.9 | 2.1 | 37.4 |
| 5 | 20.4 | 3.6 | 19.1 |
| 6 | 6.4 | 11.0 | 53.0 |
| 7 | 5.8 | 7.9 | 38.2 |
| Avg | 10.9 | 5.6 | 35.1 |
| SE | 2.0 | 1.2 | 3.9 |

TABLE V-II

% Cells in the LSP of EPC-Rich MASPC - additional surface marker combinations - Results of Individual samples after 3-day culture

| Sample No. | EPCs co-expressing Ac-LDL Uptake & Ulex lectin | EPCs co-expressing CD309 & CD202B | EPCs co-expressing CD31 & VEGFR1 |
|---|---|---|---|
| 1 | 33.8 | 2.1 | 13.6 |
| 2 | 30.4 | 13.5 | 32.8 |
| 3 | 17.7 | 12.0 | 38.5 |
| 4 | 7.6 | 0.5 | 16.7 |
| 5 | 6.4 | 1.2 | 33.3 |
| Avg | 19.2 | 5.9 | 27.0 |
| SE | 5.7 | 2.8 | 5.0 |

EXPERIMENTAL EXAMPLE 7

Characterization of MASPC-rich LSP—Clonogenic Potential

In this set of experiments, an expanded and activated population of MASPC was generated from the co-culturing of TDC together with an activated human-CBMC-derived DCP as described in hereinabove with reference to Experimental Examples 5 and 6. The cells were plated on an extracellular methylcellulose matrix gel and the cells ability for proliferation and colony formation was examined microscopically on days 1-21 of culturing in accordance with protocols described hereinabove with reference to Example 19.

Results from 5 independent experiments show that co-culturing of activated DCP and TDC typically yields LSP of EPC-rich MASPC and MASPC-rich LSP having colony forming cells (CFC), capable of generating a variety of cell colony types, at a frequency of 216+/−42.1 per 100,000 seeded cells.

Figure 2:
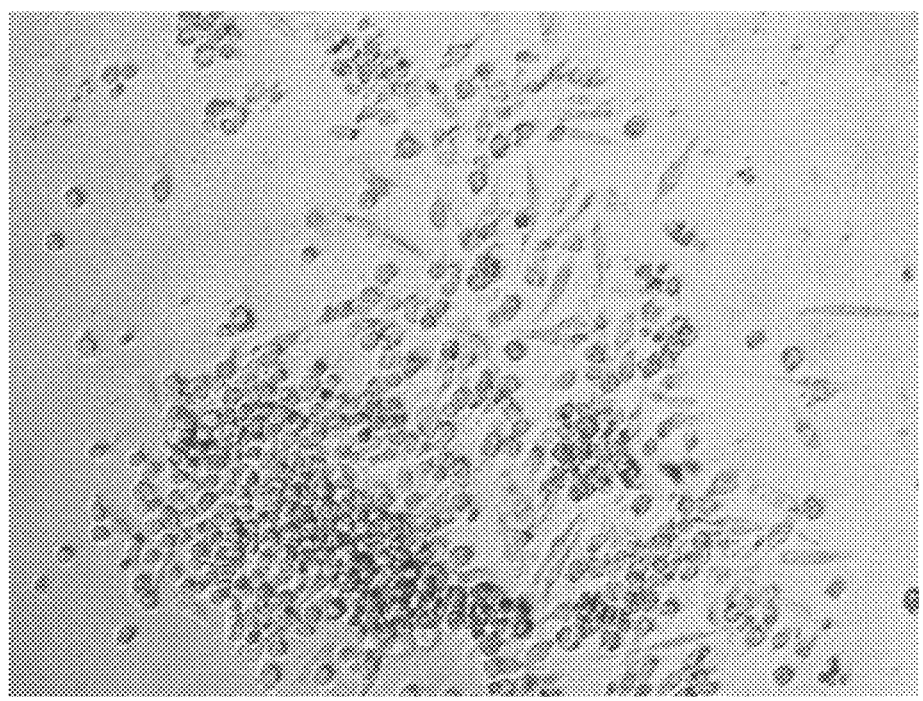
FIG. 2 is a photomicrograph showing colonies generated by CFU (colony forming units) in an expanded population of an LSP, EPC-rich MASPC, in accordance with some applications of the present invention.

Reference is made to FIG. 2, which is a photomicrograph showing slow multiplication and colony formation in an expanded and activated population of MASPC-Rich LSP generated by co-culturing of an activated human-CBMC-derived DCP together with an MASPC-rich TDC population, in accordance with some applications of the present invention. FIG. 2 shows typical colonies in the expanded and activated population of MASPC as well as elongated and spindle-shaped cells that are typical to endothelial progenitor cells (EPC). Generally, single stem/progenitor cells that are capable of proliferation generate short and long term cell colonies.

EXPERIMENTAL EXAMPLE 8

Characterization of LSP of EPC-Rich MASPC—Angiogenic Potential

In this set of experiments, an LSP of EPC-rich MASPC, was generated from the co-culturing of TDC together with an activated human-CBMC-derived DCP, in accordance with the steps described in Experimental Examples 1, 2, 3, and 4. Co-cultured cells were maintained in a medium containing at least (a) 5% autologous serum, (b) 5 IU/ml Heparin, and (c) 2-50 ng/ml IL-10 and/or 1-20 ng/ml VEGF. The medium was changed every 2-3 days. It is to be noted that for some applications, experiments may be conducted in which neither IL-10 nor VEGF is included in the medium.

The cells were then plated on an extracellular methylcellulose matrix gel, and the angiogenic pattern and vascular tube formation of the cells was examined microscopically on days 1-14 of culturing, in accordance with protocols described hereinabove with reference to Example 17.

Figure 3:
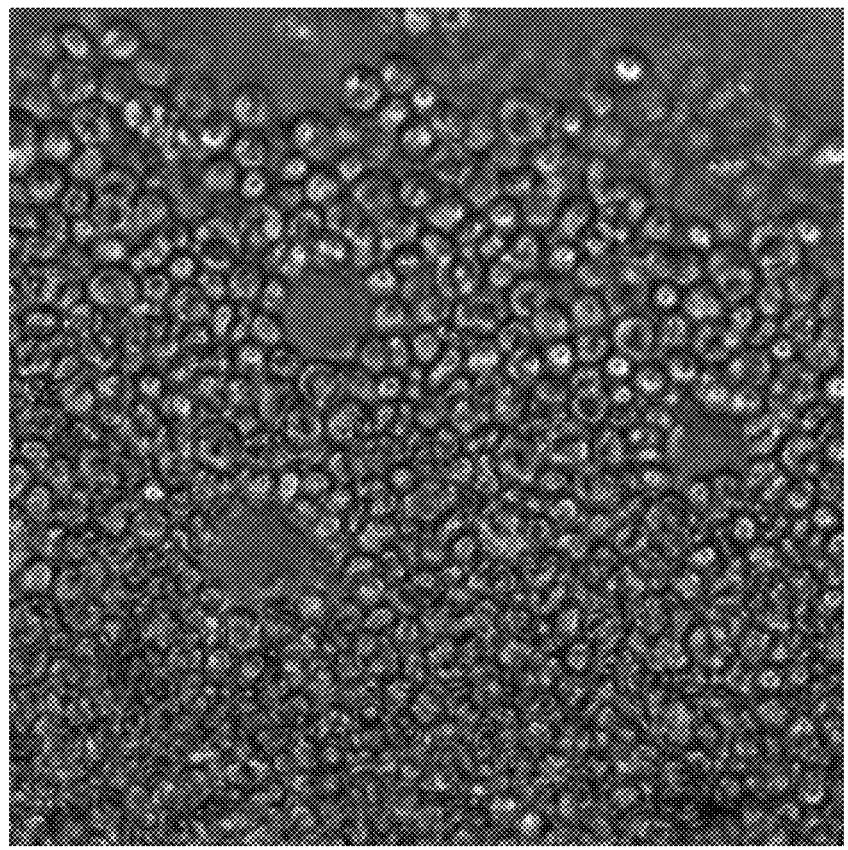
FIG. 3 is a photomicrograph showing tube formation in an LSP, EPC-rich MASPC, in accordance with some applications of the present invention.

FIG. 3 is a photomicrograph showing tube formation in EPC-rich MASPC, generated in accordance with some applications of the present invention. FIG. 3 shows typical tube formation in the LSP of EPC-Rich MASPC. As shown, formation of tube-like capillaries with some sprouting was observed and scored as grade 3.

For some applications, techniques described herein are practiced in combination with techniques described in one or more of the references cited in the present patent application.

It is to be appreciated that by way of illustration and not limitation, techniques are described herein with respect to cells derived from an animal source. The scope of the present invention includes performing the techniques described herein using a DCP, MASPC, and TDC derived from non-animal cells (e.g., plant cells), mutatis mutandis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An in vitro method for generating a lineage specific precursor/progenitor cell population (LSP) comprising:
    (a) obtaining a population of isolated immature antigen-presenting cells;
    (b) activating said population of isolated immature antigen-presenting cells to generate a population of activated antigen-presenting cells;
    (c) obtaining a population of cells comprising stem/progenitor cells and enriching for stem/progenitor cells within said population of cells to generate an enriched population of stem/progenitor cells; and
    (d) following the activating, combining the population of activated antigen-presenting cells of step (b) with the enriched population of stem/progenitor cells of step (c) to form a combined population, wherein said activated antigen-presenting cells are 2-20% of said combined population when said combined population is formed, and wherein said activated antigen-presenting cells induce at least one process in the enriched population of stem/progenitor cells of the combined population, wherein the process is selected from the group consisting of: differentiation, expansion, activation, secretion of a molecule, and expression of a marker,
    thereby generating a lineage specific precursor/progenitor population (LSP) in vitro from the enriched population of stem/progenitor cells, wherein at least one of the isolated immature antigen-presenting cells of step (a) or the population of cells comprising stem/progenitor cells of step (c) is obtained from umbilical cord blood.

2. The method according to claim 1, wherein said isolated immature antigen-presenting cells of step (a) and said population of cells comprising stem/progenitor cells of step (c) are obtained from umbilical cord blood.

3. The method according to claim 1, wherein said isolated immature antigen-presenting cells of step (a) and said population of cells comprising stem/progenitor cells of step (c) are obtained from the same umbilical cord blood sample.

4. The method according to claim 1, wherein the isolated immature antigen-presenting cells of step (a) are obtained from umbilical cord blood.

5. The method according to claim 1, wherein the population of cells comprising stem/progenitor cells of step (c) is obtained from umbilical cord blood.

6. The method according to claim 1, wherein:
    said activating step (b) comprises:
        increasing, to at least 15%, a proportion of the antigen-presenting cells in a greater population of cells that includes the antigen-presenting cells; and
        performing at least one action selected from the group consisting of: providing activation signals to the antigen-presenting cells and incubating the antigen-presenting cells for a period of 0.5 hours to 3 days before said combining step (d).

7. The method according to claim 6, wherein increasing the antigen-presenting cells to the proportion of at least 15% of the greater population comprises at least one action selected from the group consisting of:
    (a) increasing a proportion of antigen-presenting cells expressing CD141 to at least 1% of the greater population, and
    (b) increasing, to at least 5% of the greater population, antigen-presenting cells that express a marker selected from the group consisting of: CD303 and CD304.

8. The method according to claim 6, wherein said incubating comprises incubating the immature antigen-presenting cells for a period of 0.5 hours to 22 hours.

9. The method according to claim 1, wherein said activating step (b) comprises incubating the immature antigen-presenting cells in a medium including at least one component selected from the group consisting of: IL-10, IL-12, IL-18, IL-27, TGF beta, bFGF, and VEGF.

10. The method according to claim 9, wherein said activating step (b) comprises incubating the immature antigen-presenting cells in a medium including at least one component selected from the group consisting of: IL-10 and VEGF.

11. The method according to claim 1,
    wherein step (a) comprises:
        freezing at least 100 million mononuclear cells;
        thawing the frozen cells; and
        obtaining said population of isolated immature antigen-presenting cells from the thawed cells, and
    wherein said population of cells comprising stem/progenitor cells of step (c) is obtained from said thawed cells.

* * * * *